(12) United States Patent
Cheung

(10) Patent No.: US 7,422,997 B2
(45) Date of Patent: Sep. 9, 2008

(54) METHOD TO ENHANCE PLANT GROWTH WITH A BIOLOGICAL FERTILIZER COMPOSITION COMPRISING POULTRY MANURE AND ELECTROMAGNETIC FIELD TREATED YEASTS

(75) Inventor: Ling Yuk Cheung, Hong Kong (HK)

(73) Assignee: Ultra Biotech Limited, Douglas (IM)

( * ) Notice: Subject to any disclaimer, the term of this patent is extended or adjusted under 35 U.S.C. 154(b) by 215 days.

(21) Appl. No.: 11/233,268

(22) Filed: Sep. 21, 2005

(65) Prior Publication Data

US 2006/0024281 A1 Feb. 2, 2006

Related U.S. Application Data

(60) Continuation of application No. 10/625,056, filed on Jul. 22, 2003, now Pat. No. 6,979,444, which is a division of application No. 09/796,818, filed on Mar. 1, 2001, now Pat. No. 6,596,272.

(51) Int. Cl.
*A01N 63/04* (2006.01)
*A01N 63/00* (2006.01)
*A01N 59/00* (2006.01)
*C12N 13/00* (2006.01)
*C12N 1/16* (2006.01)
*C12N 1/18* (2006.01)
*A01N 57/00* (2006.01)

(52) U.S. Cl. .............. 504/117; 424/93.51; 435/173.1; 435/254.2; 504/118; 504/121; 504/123; 504/127

(58) Field of Classification Search .............. 504/117, 504/118, 121, 123, 127; 424/93.51; 435/173.1, 435/254.2
See application file for complete search history.

(56) References Cited

U.S. PATENT DOCUMENTS

| | | | |
|---|---|---|---|
| 2,107,830 A | 2/1938 | Liebesny et al. | |
| 3,711,392 A | 1/1973 | Betzger | |
| 3,870,599 A | 3/1975 | Azarowicz | |
| 3,968,254 A | 7/1976 | Rhodes et al. | |
| 4,041,182 A | 8/1977 | Erickson et al. | |
| 4,119,429 A | 10/1978 | Lovness | |
| 4,155,737 A | 5/1979 | Dommergues et al. | |
| 4,348,483 A | 9/1982 | Skogerson | |
| 4,952,229 A | 8/1990 | Muir | |
| 4,985,060 A | 1/1991 | Higa | |
| 5,071,462 A | 12/1991 | Kimmra | |
| 5,082,936 A | 1/1992 | James et al. | |
| 5,312,632 A | 5/1994 | Simsa et al. | |
| 5,534,437 A * | 7/1996 | Arrau .................. | 435/290.3 |
| 5,578,486 A * | 11/1996 | Zhang .................. | 435/243 |
| 5,952,020 A | 9/1999 | Lizak | |
| 5,981,219 A | 11/1999 | Flugge et al. | |
| 6,143,731 A | 11/2000 | James et al. | |
| 6,159,510 A | 12/2000 | Lizak | |
| 6,391,617 B1 | 5/2002 | Cheung | |
| 6,391,618 B1 | 5/2002 | Cheung | |
| 6,391,619 B1 | 5/2002 | Cheung | |
| 6,416,982 B1 | 7/2002 | Zhang | |
| 6,416,983 B1 | 7/2002 | Cheung | |
| 6,436,695 B1 | 8/2002 | Cheung | |
| 6,440,713 B1 | 8/2002 | Cheung | |
| 6,596,272 B2 | 7/2003 | Cheung | |
| 6,596,273 B2 | 7/2003 | Cheung | |
| 6,649,383 B1 | 11/2003 | Cheung | |
| 6,660,508 B1 | 12/2003 | Cheung | |
| 6,709,849 B2 | 3/2004 | Cheung | |
| 6,753,008 B2 | 6/2004 | Cheung | |
| 6,756,050 B2 | 6/2004 | Cheung | |
| 6,759,055 B2 | 7/2004 | Cheung | |
| 6,761,886 B2 | 7/2004 | Cheung | |
| 6,793,933 B2 | 9/2004 | Cheung | |
| 6,800,466 B2 | 10/2004 | Cheung | |
| 6,828,131 B2 | 12/2004 | Zhang | |
| 2002/0123127 A1 | 9/2002 | Cheung | |
| 2002/0123129 A1 | 9/2002 | Cheung | |
| 2002/0123130 A1 | 9/2002 | Cheung | |
| 2003/0064487 A1 | 4/2003 | Zhang | |
| 2003/0230126 A1 | 12/2003 | Cheung | |
| 2003/0230245 A1 | 12/2003 | Cheung | |
| 2003/0232038 A1 | 12/2003 | Cheung | |
| 2003/0232039 A1 | 12/2003 | Cheung | |
| 2003/0232059 A1 | 12/2003 | Cheung | |
| 2003/0235565 A1 | 12/2003 | Cheung | |
| 2003/0235566 A1 | 12/2003 | Cheung | |
| 2003/0235567 A1 | 12/2003 | Cheung | |
| 2003/0235568 A1 | 12/2003 | Cheung | |
| 2003/0235569 A1 | 12/2003 | Cheung | |
| 2003/0235570 A1 | 12/2003 | Cheung | |
| 2004/0001812 A1 | 1/2004 | Cheung | |

(Continued)

FOREIGN PATENT DOCUMENTS

BE 1011133 5/1999

(Continued)

OTHER PUBLICATIONS

Bassett. 1993. Beneficial effects of electromagnetic fields. J Cell Biochem. 51(4):387-93.

(Continued)

*Primary Examiner*—Jon P Weber
*Assistant Examiner*—Kailash C Srivastava
(74) *Attorney, Agent, or Firm*—Jones Day

(57) ABSTRACT

The present invention provides a method to enhance plant growth with a biological fertilizer composition that comprises yeast cells and poultry manure. The yeast cells of the invention have an enhanced ability to fix atmospheric nitrogen, decompose phosphorus minerals and compounds, decompose potassium minerals and compounds, decompose complex carbon compounds, overproduce growth factors, overproduce adenosine triphosphate, decompose undesirable chemicals, suppress growth of pathogenic microorganisms, or reduce undesirable odor.

22 Claims, 11 Drawing Sheets

U.S. PATENT DOCUMENTS

Figure 1:
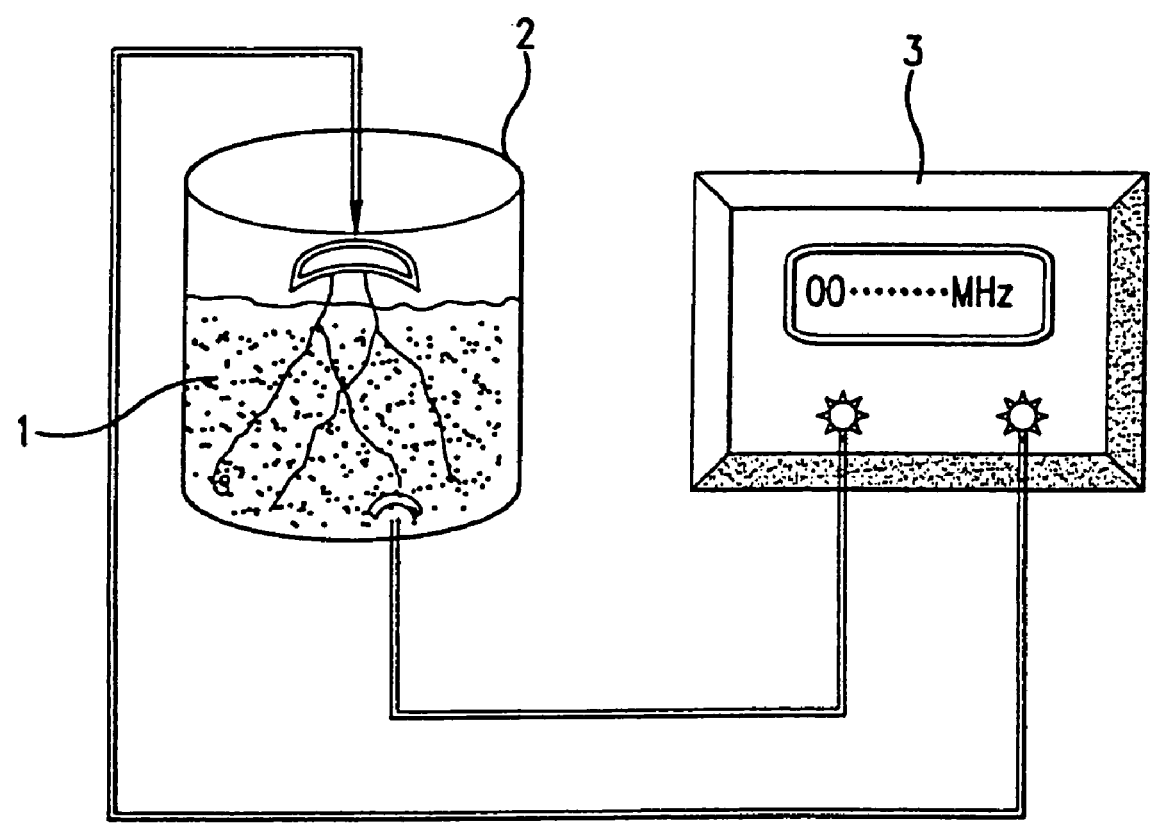

| | | |
|---|---|---|
| 2004/0001813 A1 | 1/2004 | Cheung |
| 2004/0001814 A1 | 1/2004 | Cheung |
| 2004/0001857 A1 | 1/2004 | Cheung |
| 2004/0001859 A1 | 1/2004 | Cheung |
| 2004/0005335 A1 | 1/2004 | Cheung |
| 2004/0005336 A1 | 1/2004 | Cheung |
| 2004/0005680 A1 | 1/2004 | Cheung |
| 2004/0168492 A1 | 9/2004 | Cheung |
| 2004/0253252 A1 | 12/2004 | Cheung |
| 2004/0253253 A1 | 12/2004 | Cheung |
| 2004/0253254 A1 | 12/2004 | Cheung |
| 2004/0253255 A1 | 12/2004 | Cheung |
| 2004/0253256 A1 | 12/2004 | Cheung |
| 2004/0253257 A1 | 12/2004 | Cheung |
| 2004/0253258 A1 | 12/2004 | Cheung |
| 2004/0253259 A1 | 12/2004 | Cheung |
| 2004/0253260 A1 | 12/2004 | Cheung |
| 2004/0253261 A1 | 12/2004 | Cheung |
| 2004/0253262 A1 | 12/2004 | Cheung |
| 2004/0253263 A1 | 12/2004 | Cheung |
| 2004/0253264 A1 | 12/2004 | Cheung |
| 2004/0253265 A1 | 12/2004 | Cheung |
| 2004/0253266 A1 | 12/2004 | Cheung |
| 2004/0253267 A1 | 12/2004 | Cheung |
| 2004/0253268 A1 | 12/2004 | Cheung |
| 2004/0256251 A1 | 12/2004 | Cheung |
| 2004/0265990 A1 | 12/2004 | Cheung |
| 2005/0106166 A1 | 5/2005 | Cheung |
| 2005/0106167 A1 | 5/2005 | Cheung |
| 2005/0106168 A1 | 5/2005 | Cheung |
| 2005/0106169 A1 | 5/2005 | Cheung |
| 2005/0106170 A1 | 5/2005 | Cheung |
| 2005/0106171 A1 | 5/2005 | Cheung |
| 2005/0106172 A1 | 5/2005 | Cheung |
| 2005/0106173 A1 | 5/2005 | Cheung |
| 2005/0106174 A1 | 5/2005 | Cheung |
| 2005/0106704 A1 | 5/2005 | Cheung |
| 2005/0106705 A1 | 5/2005 | Cheung |
| 2005/0150264 A1 | 7/2005 | Cheung |
| 2005/0155400 A1 | 7/2005 | Cheung |

FOREIGN PATENT DOCUMENTS

| | | |
|---|---|---|
| CA | 1077290 | 5/1980 |
| CA | 1103176 | 6/1981 |
| CN | 1081662 | 2/1994 |
| CN | 1082016 | 2/1994 |
| CN | 1082017 | 2/1994 |
| CN | 1102635 | 5/1995 |
| CN | 1103060 | 5/1995 |
| CN | 1109595 | 10/1995 |
| CN | 1110317 | 10/1995 |
| CN | 1207873 | 2/1999 |
| EP | 553 377 | 8/1993 |
| ES | 475500 | 11/1978 |
| FR | 2 222 433 | 10/1974 |
| FR | 2 489 363 | 3/1982 |
| HU | 33012 | 10/1984 |
| JP | 60 028893 | 2/1985 |
| SU | 220 916 | 3/1967 |
| SU | 1722364 | 3/1992 |
| SU | 1750570 | 7/1992 |
| WO | WO 87/02705 | 5/1987 |
| WO | WO 95/04814 | 2/1995 |
| WO | WO 02/070436 | 9/2002 |
| WO | WO 02/070682 | 9/2002 |
| WO | WO 02/070683 | 9/2002 |

OTHER PUBLICATIONS

Binninger et al. 1997. Effects of 60Hz AC magnetic fields on gene expression following exposure over multiple cell generations using *Saccharomyces cerevisiae*. Bioelectrochemistry and Bioenergetics 43(1):83-89.

Bugbee et al. 1998. Leaching of nitrogen and phosphorus from potting media containing biosolids compost as affected by organic and clay amendments. Bull Environ Contam Toxicol. 60(5):716-23.

Gonzalez et al. 1980. Effects of an electric field of sinusoidal waves on the amino acid biosynthesis by *Azotobacter*. Z. Naturforsch. 35c:258-61.

Goodman et al. 1995. Effects of electromagnetic fields on molecules and cells. International Review of Cytology. Eds. Kwang et al. Academic Press, vol. 158, p. 279-339.

Greweling et al. 1960. Chemical soil tests. Cornell Experiment Station Bulletin, 960:22-25.

Grospietsch et al. 1995. Stimulating effects of modulated 150 MHz electromagnetic fields on the growth of *Escherichia coli* in a cavity resonator. Bioelectrochemistry and Bioenergetics. 37:17-23.

Grundler et al. 1982. Resonant like dependence of yeast growth rate on microwave frequencies. Br J Cancer Suppl. 45(5):206-8.

Grundler et al. Mechanisms of electromagnetic interaction with cellular systems. Naturwissenschafter 79:551-559.

Grundler. 1978. Nonthermal effects of millimeter microwaves on yeast growth. Z Naturforsch. 33c:15-22.

Grundler. 1989. Resonant microwave effect on locally fixed yeast microcolonies. Z Naturforsch. 44c:863-66.

Hsui-Che et al. 1994. Experimental Results of TLB in Tropical Country-Malaysia. Academic Theses on TLB Complex Microbial Fertilizer. Zhang, LY. eds. China Science and Technology Press. pp. 104-126.

Lin et al. 1994. Specific region of the c myc promoter is responsive to electric and magnetic fields. J Cell Biochem. 54(3):281-8.

Lunt et al. 1950. The Morgan soil testing system. Connecticut Agricultural Experiment Station, New Haven, Connecticut. Bulletin 541.

Moore. 1979. Biological effects of magnetic fields: studies with microorganisms. Can J Microbiol. 25:1145-51.

Murphy et al. 1962. A modified single solution method for the determination of phosphate in natural waters. Anal Chem Acta. 27:31-36.

Norris et al. 1997. Do bacteria sing? Sonic intercellular communication between bacteria may reflect electromagnetic intracellular communication involving coherent collective vibrational modes that could integrate enzyme activities and gene expression. Mol Microbiol. 24(4):879-80.

Phillips. 1993. Effects of electromagnetic field exposure on gene transcription. J Cell Biochem. 51(4):381-6.

Pichiko et al. Electromagnetic stimulation of productivity of microorganisms and its mechanisms. Prikladnaya Biokhimiya I Mikrobiologiya 32(4):468-472 [in Ukrainian with English Abstract].

Puchyr et al. 1986. Determination of trace elements in foods by HCl-HNO3 leaching and flame atomic absorption spectroscopy. J Assoc Off Anal Chem. 69(5):868-70.

Romano-Spica et al. 2000. Ets1 oncogene induction by ELF modulated 50 MHz radiofrequency electromagnetic field. Bioelectromagnetics. 21(1):8-18.

Saha et al. 1999. Microbial Manipulation of Rumen Fermentation Using *Saccharomyces cerevisiae* as Probiotics. Current Science (Bangalore) 77(5):696-97.

Van Rensburg et al. 1998. Engineering yeast for efficient cellulose degradation. Yeast. 14(1):67-76.

Verhasselt et al. 1995. New open reading frames, one of which is similar to the nifV gene of *Azotobacter vinelandii*, found on a 12.5 kbp fragment of chromosome IV of *Saccharomyces cerevisiae*. Yeast. 11(10):961-6.

Zhang et al. 1992. Electrostimulation of the dehydrogenase system of yeast by alternating currents. Bioelectrochemistry and Bioenergetics. 28:341-53.

Zhang. 1994. Introduction to TLB, A Complex Microbial Fertilizer-Preliminary Application of MAB in Agriculture. Academic Theses on TLB Complex Microbial Fertilizer. Zhang, LY. eds. China Science and Technology Press. p. 1-17 [in Chinese with English Abstract].

* cited by examiner

METHOD TO ENHANCE PLANT GROWTH WITH A BIOLOGICAL FERTILIZER COMPOSITION COMPRISING POULTRY MANURE AND ELECTROMAGNETIC FIELD TREATED YEASTS

This application is a continuation of U.S. application Ser. No. 10/625,056, filed Jul. 22, 2003, now U.S. Pat. No. 6,979,444 which is a divisional of U.S. application Ser. No. 09/796,818, filed Mar. 1, 2001, now U.S. Pat. No. 6,596,272, issued on Jul. 22, 2003, the entire disclosure of each of which is incorporated herein by reference in its entirety.

1. FIELD OF THE INVENTION

The invention relates to biological fertilizers that comprise yeasts and an organic substrate. The yeasts in the compositions of the invention have been stimulated to perform a variety of functions including the conversion of the organic materials into non-hazardous plant nutrients. The invention also relates to methods for manufacturing biological fertilizers, and methods for using the biological fertilizers to increase crop yields.

2. BACKGROUND OF THE INVENTION

Use of fertilizer is essential in supporting the growth of high yield crops. Of the basic nutrients that plants need for healthy growth, large amounts of nitrogen (taken up as $NO_3^-$ or $NH_4^+$), phosphorus (taken up as $H_2PO_4^-$), and potassium (taken up as $K^+$) nutrients are required by most crops on most soils (Wichmann, W., et al., IFA World Fertilizer Use Manual). Such large amounts of nitrogen, phosphorus, and potassium nutrients are supplied mainly in the form of mineral fertilizers, either processed natural minerals or manufactured chemicals (K. F. Isherwood, 1998, Mineral Fertilizer Use and the Environment, United Nations Environmental Programme Technical Report No. 26).

Despite the importance of mineral fertilizers in providing mankind with abundant agricultural products, the harm done to the environment has been recognized in recent years. Mineral fertilizers may incurred damages to soils. For example, most nitrogen fertilizers may acidify soils, thereby adversely affecting the growth of plants and other soil organisms. Extensive use of chemical nitrogen fertilizers may also inhibit the activity of natural nitrogen fixing microorganisms, thereby decreasing the natural fertility of soils. The long term use of mineral fertilizers may also cause severe environmental pollution. For example, the loss of nitrogen and phosphate fertilizers due to leaching and soil erosion has led to contamination of soil and ground water, and eutrophication of surface water. Cleaning up polluted soil and water has been a complicated and difficult task. The cost for such a task is also astronomical.

In search for a solution to the problem, some are going back to organic fertilizers, such as manure (Wichmann, W., et al., IFA World Fertilizer Use Manual). The use of manure as fertilizer dates to the beginnings of agriculture. Large amounts of manure are produced by livestock. For example, in the United States, farms (including confined animal feeding operations) generate more than 136 million metric tons (dry weight basis) of waste products annually. Manure has value in maintaining and improving soil because of the plant nutrients, humus, and organic substances contained in it. Studies have shown that a high percentage of the nitrogen, phosphorus, and potassium fed to dairy cattle are excreted in manure.

As manure must be managed carefully in order to derive the most benefit from it, some farmers may be unwilling to expend the necessary time and effort. Manure must be carefully stored to minimize loss of nutrients. It must be applied to the right kind of crop at the proper time. In general, manure does not provide all the plant nutrients needed and very large amount of organic fertilizers have to be applied to soil. Thus, there is a tendency to discount the value of manure as fertilizer. Manure may also contain undesirable chemicals, such as antibiotics and hormones. Only in underdeveloped countries, where artificial fertilizer may be costly or unavailable and where labor is relatively cheap, manure is attractive as a fertilizer.

Furthermore, manure may contain significant levels of nitrogen and phosphorous which threaten water resources if not managed correctly. If not stored or disposed of properly, it can pose health and environmental threats. For example, it can cause air pollution, i.e., odor and dust; and contamination of surface and ground water with excess nutrients, organic matter, salts, and pathogens. For example, manure contains pathogenic microorganisms, such as *Escherichia coli, Salmonella* spp., *Shigella* spp., and *Campylobacter jejuni*.

Biological fertilizers utilizing microorganisms have been proposed as alternatives to mineral fertilizers. Naturally occurring nitrogen fixing microorganisms including bacteria, such as *Rhizobium, Azotobacter*, and *Azospirillum*, (See for example, U.S. Pat. No. 5,071,462) and fungi, such as *Aspergillus flavus-oryzae*, (See, for example, U.S. Pat. No. 4,670,037) have been utilized in biological fertilizers. Naturally occurring microorganisms capable of solubilizing phosphate rock ore or other insoluble phosphates into soluble phosphates have also been utilized in biological fertilizers either separately (e.g., U.S. Pat. No. 5,912,398) or in combination with nitrogen fixing microorganisms (e.g., U.S. Pat. No. 5,484,464). Genetically modified bacterial strains have also been developed and utilized in biological fertilizers. An approach based on recombinant DNA techniques has been developed to create more effective nitrogen fixing, phosphorus decomposing, and potassium decomposing bacterial strains for use in a biological fertilizer, see, for example, U.S. Pat. No. 5,578,486; PCT publication WO 95/09814; Chinese patent publication: CN 1081662A; CN 1082016A; CN 1082017A; CN 1103060A; and CN 1109595A.

However, the biological fertilizers that are based on naturally occurring microorganisms are generally not efficient enough to effectively replace mineral fertilizers. It is therefore important to develop more advanced biological fertilizers that can replace mineral fertilizers in supplying nitrogen, phosphorus, and potassium to crops for producing high quality agricultural products while avoiding the problems associated with mineral fertilizers.

The present invention provides a biological fertilizer based on non-recombinant yeasts, which can replace mineral fertilizers and provide an effective and environmentally-friendly method of using certain organic materials.

Citation of documents herein is not intended as an admission that any of the documents cited herein is pertinent prior art, or an admission that the cited documents are considered material to the patentability of the claims of the present application. All statements as to the date or representations as to the contents of these documents are based on the information available to the applicant and does not constitute any admission as to the correctness of the dates or contents of these documents.

3. SUMMARY OF THE INVENTION

The present invention relates to biological fertilizer compositions. The biological fertilizer compositions of the invention comprises up to nine different yeast cell components, poultry manure, and optionally an inorganic substrate component. In particular, the yeast cell components of the composition are each capable of at least one of the following ten functions, namely, fixing atmospheric nitrogen, decomposing insoluble phosphorus or potassium minerals, maintaining a balance of phosphorus compounds in the microenvironment, decomposing complex carbon-containing materials or compounds, overproducing growth factors, overproducing ATP, suppression of growth of pathogenic microorganisms, breakdown of undesirable chemicals, and reducing the odor of organic matters, respectively. The yeast cell components of the invention can be used as an additive which is mixed with poultry manure to form a biological fertilizer.

In one embodiment, the biological fertilizer compositions of the invention are produced by mixing poultry manure with at least seven and up to nine yeast cell components, wherein the cells of six yeast cell components perform the basic functions of fixing atmospheric nitrogen, decomposing phosphorus-containing minerals or maintaining in its immediate surroundings a balance of phosphorus compounds, decomposing potassium-containing minerals, decomposing complex carbon-containing materials or compounds, overproducing growth factors, and overproducing ATP, and wherein the cells of the other component(s) perform the supplementary functions of suppressing growth of pathogenic microorganisms, decomposing undesirable chemicals, and reducing the odor of the organic substrate in the fertilizer composition.

In preferred embodiments, the present invention uses yeasts that are commercially available and/or accessible to the public, such as but not limited to *Saccharomyces cerevisiae*. Generally, the yeast cell components of the invention are produced by culturing the pluralities of yeast cells under activation conditions such that the abilities of the pluralities of cells to perform the functions are activated or enhanced. Accordingly, in another embodiment, the invention encompasses methods of activating or enhancing the abilities of yeast cells to perform one of the ten functions. The invention also relates to methods for manufacturing the fertilizer comprising mixing poultry manure with the yeast cells of the present invention, followed by drying and packing the final product.

The invention further relates to methods for using the fertilizer compositions of the present invention. The biological fertilizer compositions of the present invention are used to support and enhance the growth and maturation of a wide variety of plants.

4. BRIEF DESCRIPTION OF FIGURES

FIG. 1 Activation of yeast cells. 1 yeast cell culture; 2 container; 3 electromagnetic field source.

Figure 2:
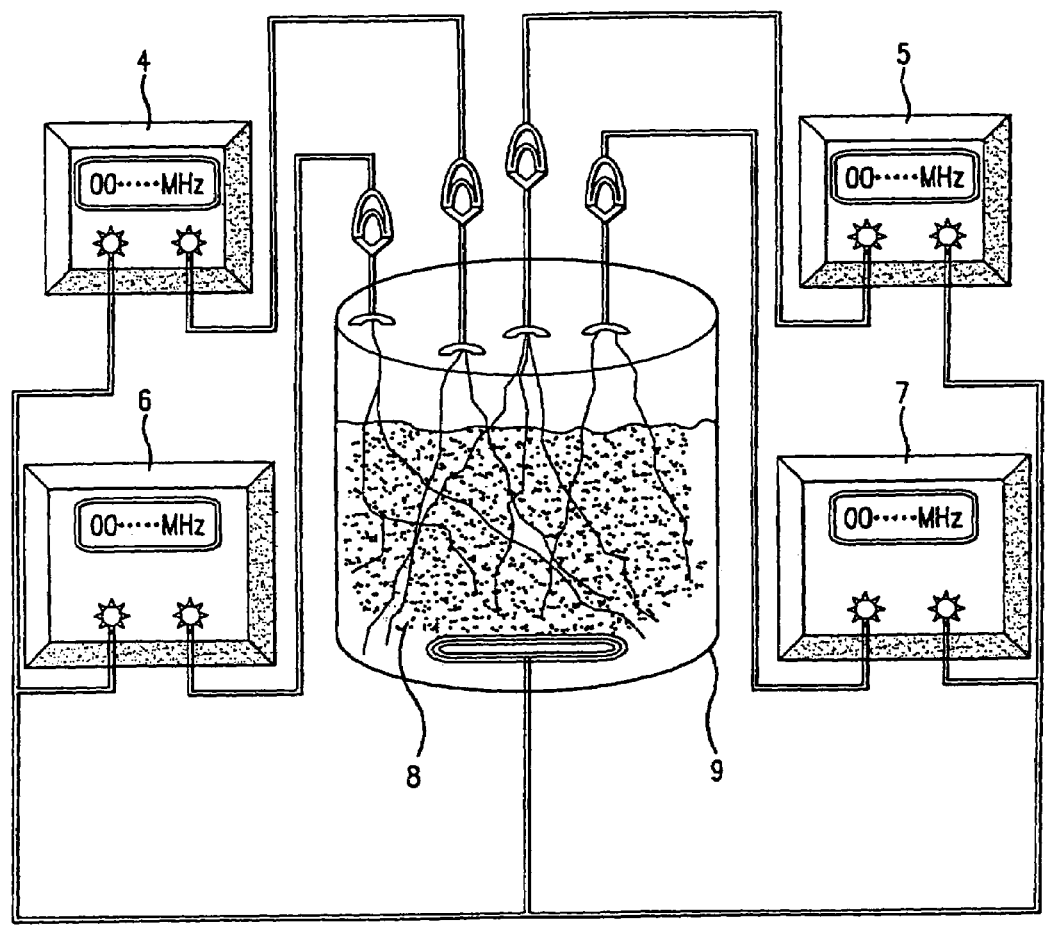

FIG. 2. Formation of symbiosis-like relationships among strains of yeasts. 4 electromagnetic field source for nitrogen-fixing yeasts; 5 electromagnetic field source for P-decomposing yeasts; 6 electromagnetic field source for K-decomposing yeasts; 7 electromagnetic field source for C-decomposing yeasts; 8 yeast cell culture; 9 container.

Figure 3:
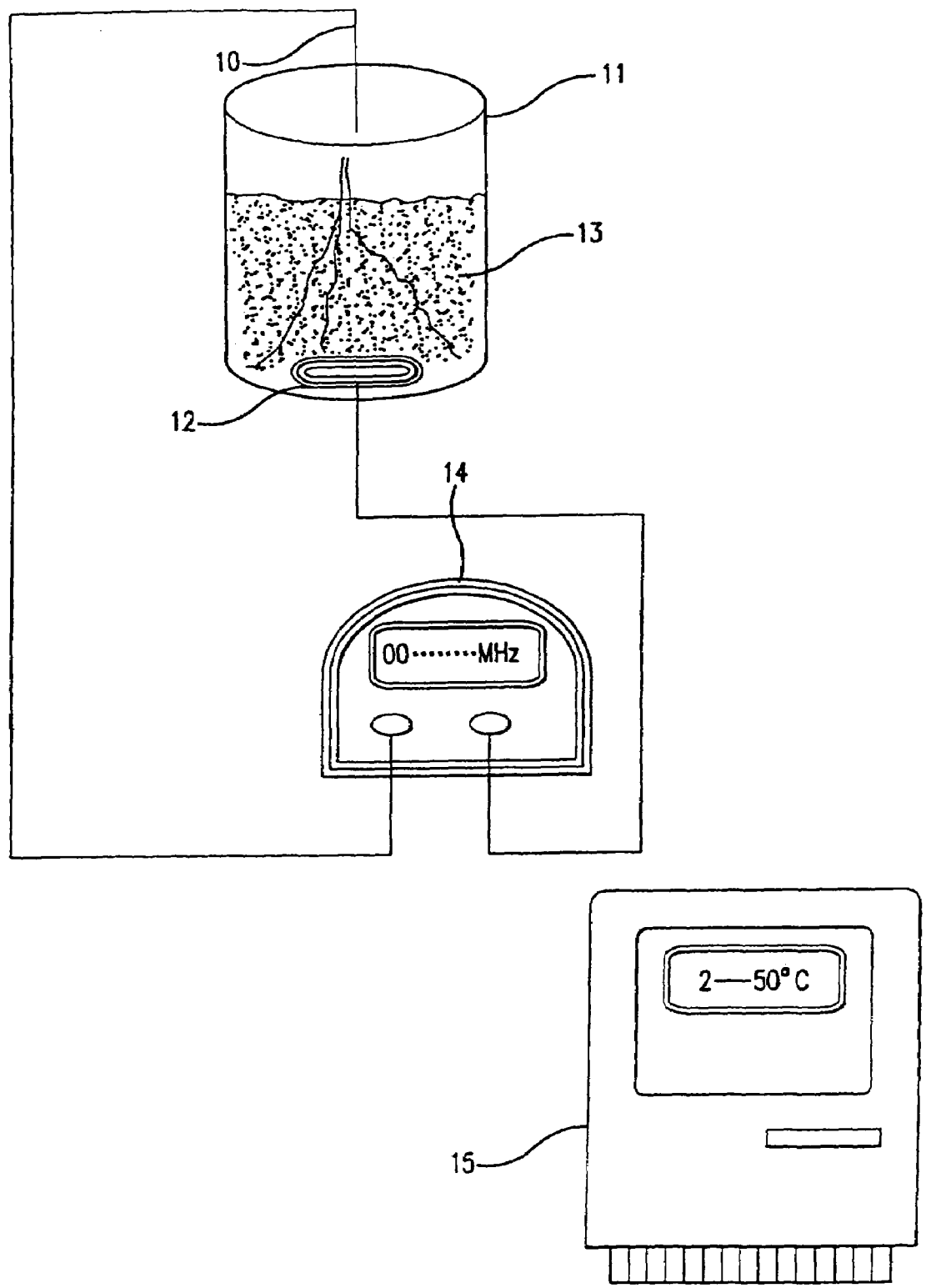

FIG. 3. Adaptation of yeast cells to a soil type. 10 electrode; 11 container; 12 electrode; 13 yeast cell culture; 14 electromagnetic field source; 15 temperature controller.

Figure 4:
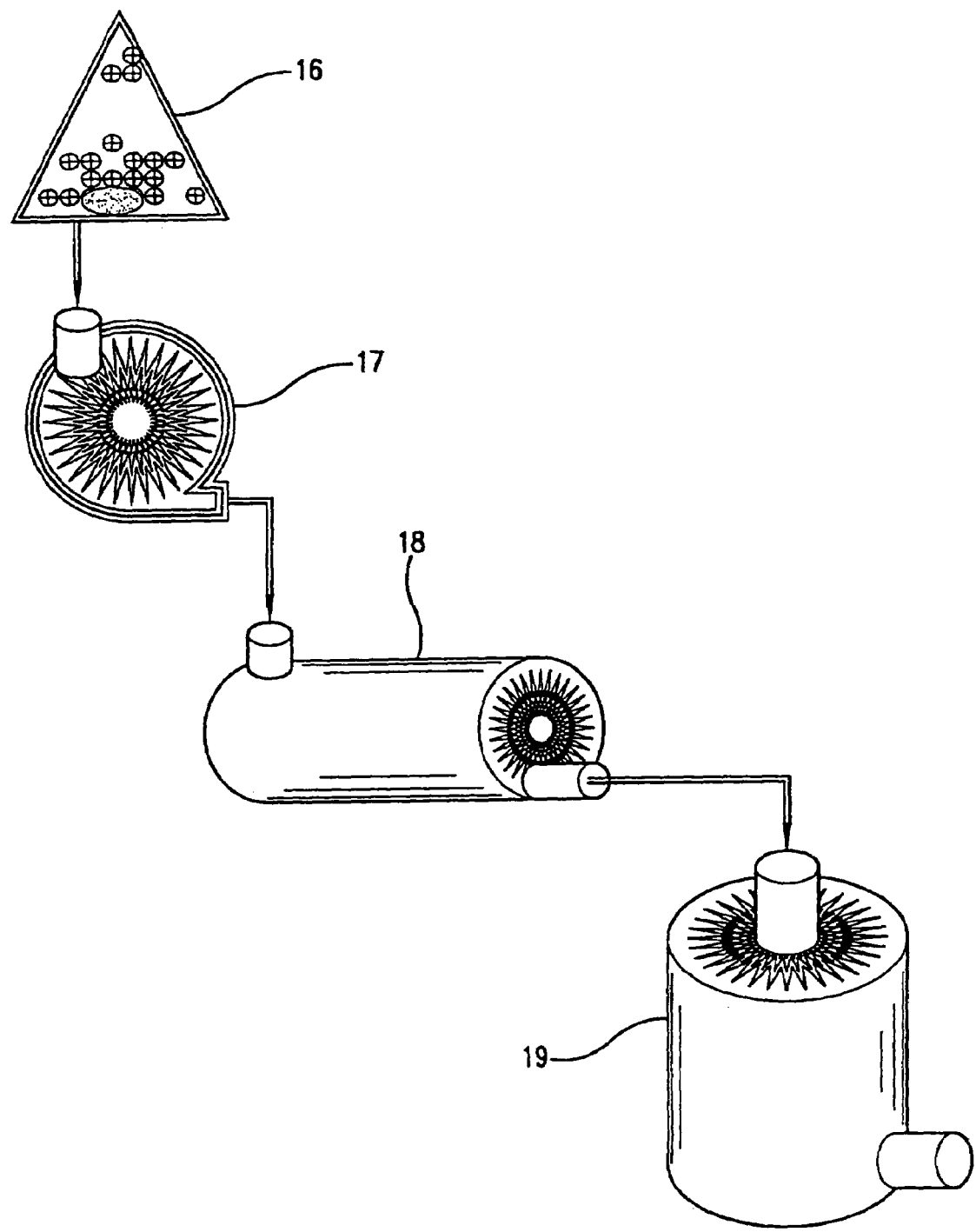

FIG. 4. Organic substrate grinding process. 16 organic raw material; 17 crusher; 18 grinder; 19 organic substrate in powder form.

Figure 5:
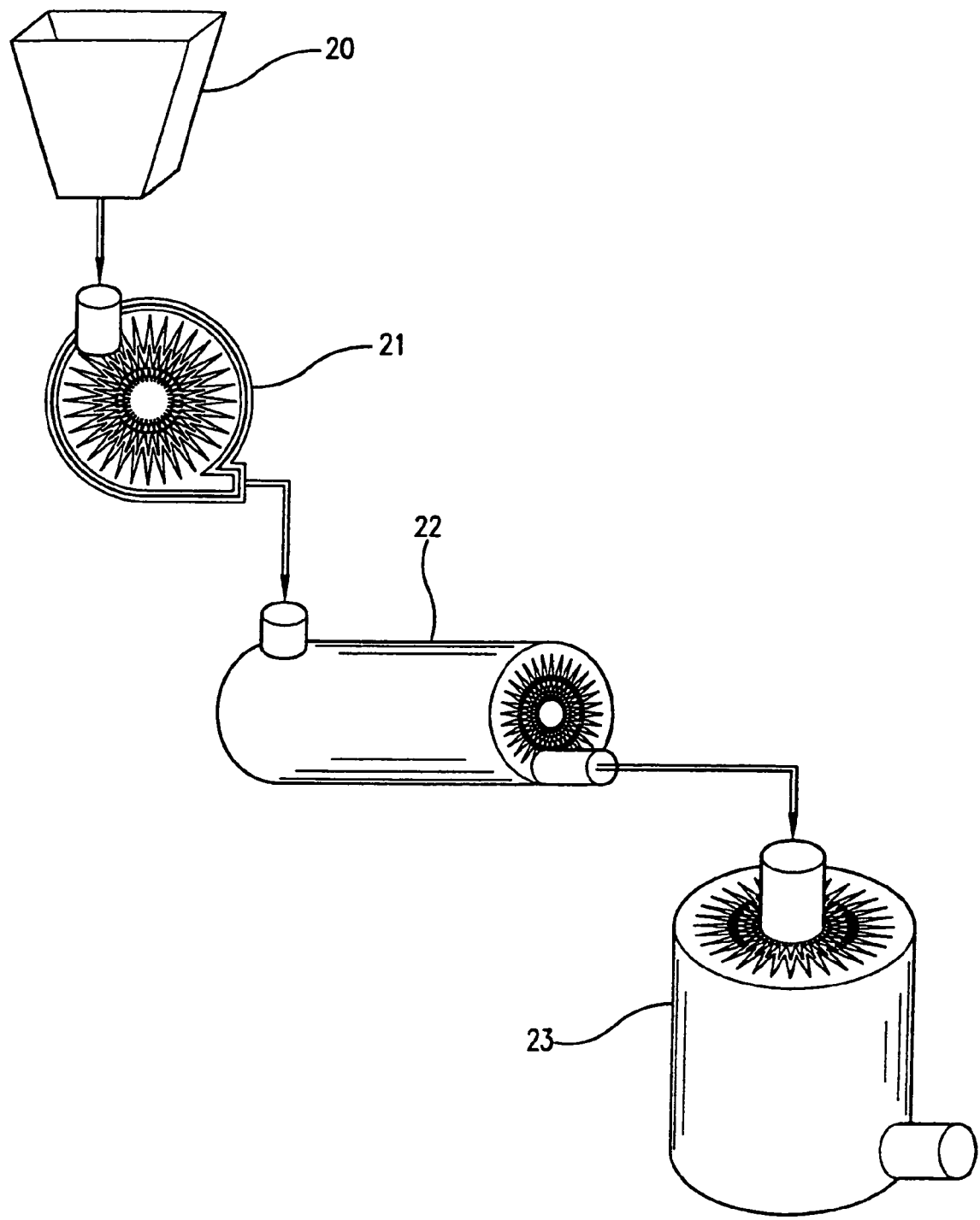

FIG. 5. Inorganic substrate grinding process. 20 inorganic raw material; 21 crusher; 22 grinder; 23 inorganic substrate in powder form.

Figure 6:
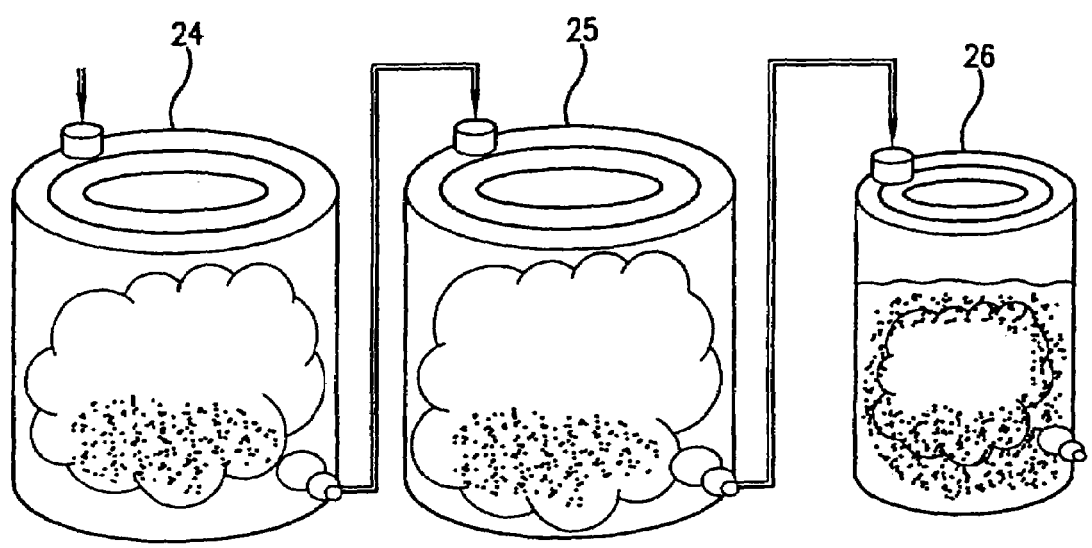

FIG. 6. Yeast fermentation process. 24 activated yeast cells; 25 tank for culturing yeast cells, starch: water ($35°$ C.)=1:2.5, semi-aerobic fermentation at 28 to $30°$ C.; 26 harvested culture.

Figure 7:
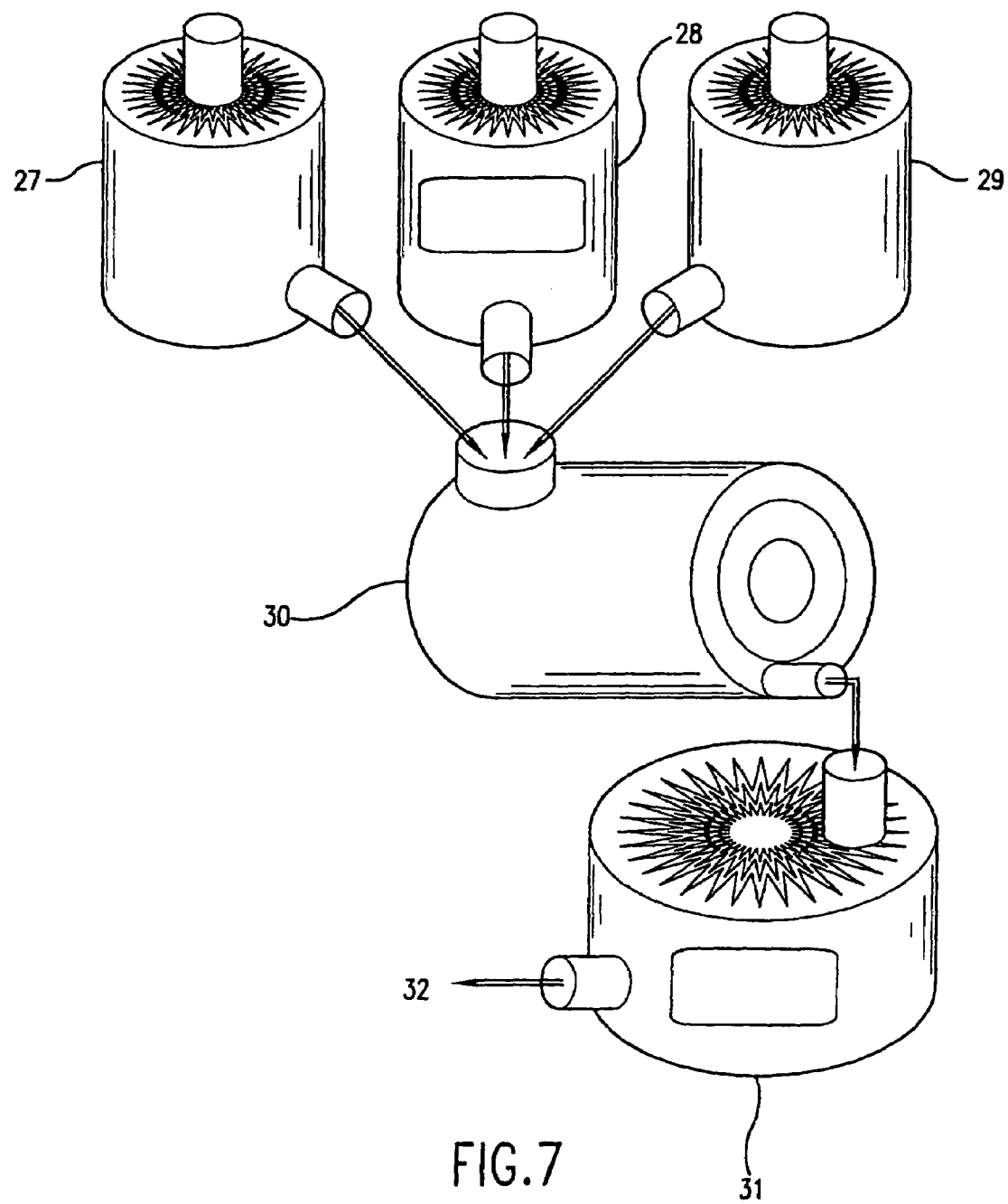

FIG. 7. Mixing organic and inorganic raw materials. 27 inorganic materials; 28 starch; 29 organic materials; 30 mixer; 31 mixture; 32 mixture to be transported to fertilizer production stage.

Figure 8:
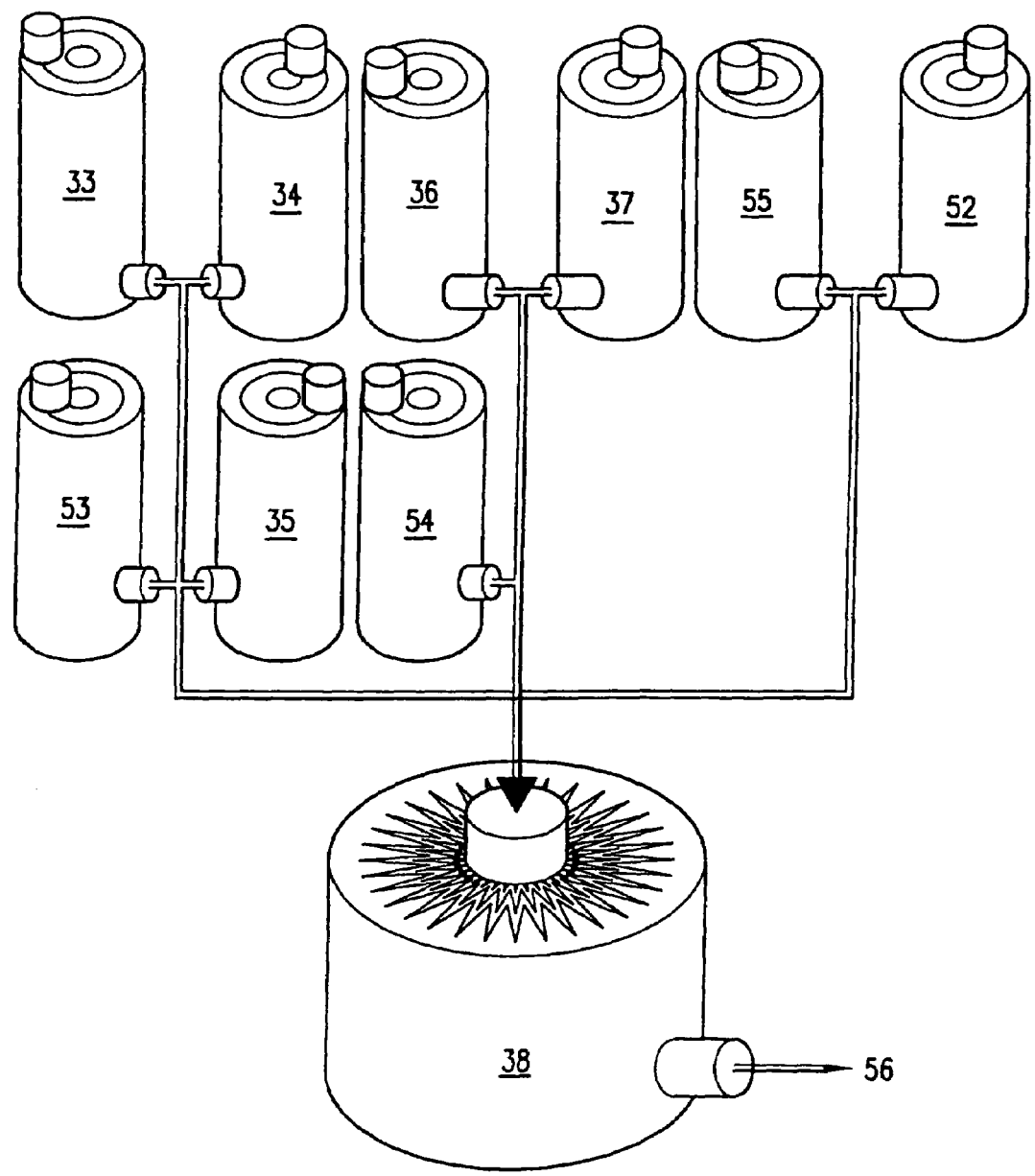

FIG. 8. Mixing yeast cells. 33 nitrogen-fixing yeasts 34 P-decomposing yeasts; 37 K-decomposing yeasts; 55 C-decomposing microbes; 35 ATP-producing yeasts; 36 GF-producing yeasts; 52 pathogen-suppressing yeasts; 53 yeasts that decompose undesirable chemicals; 54 deodorizing yeasts; 38 mixture of yeasts; 56 mixture to be transported to fertilizer production stage.

Figure 9:
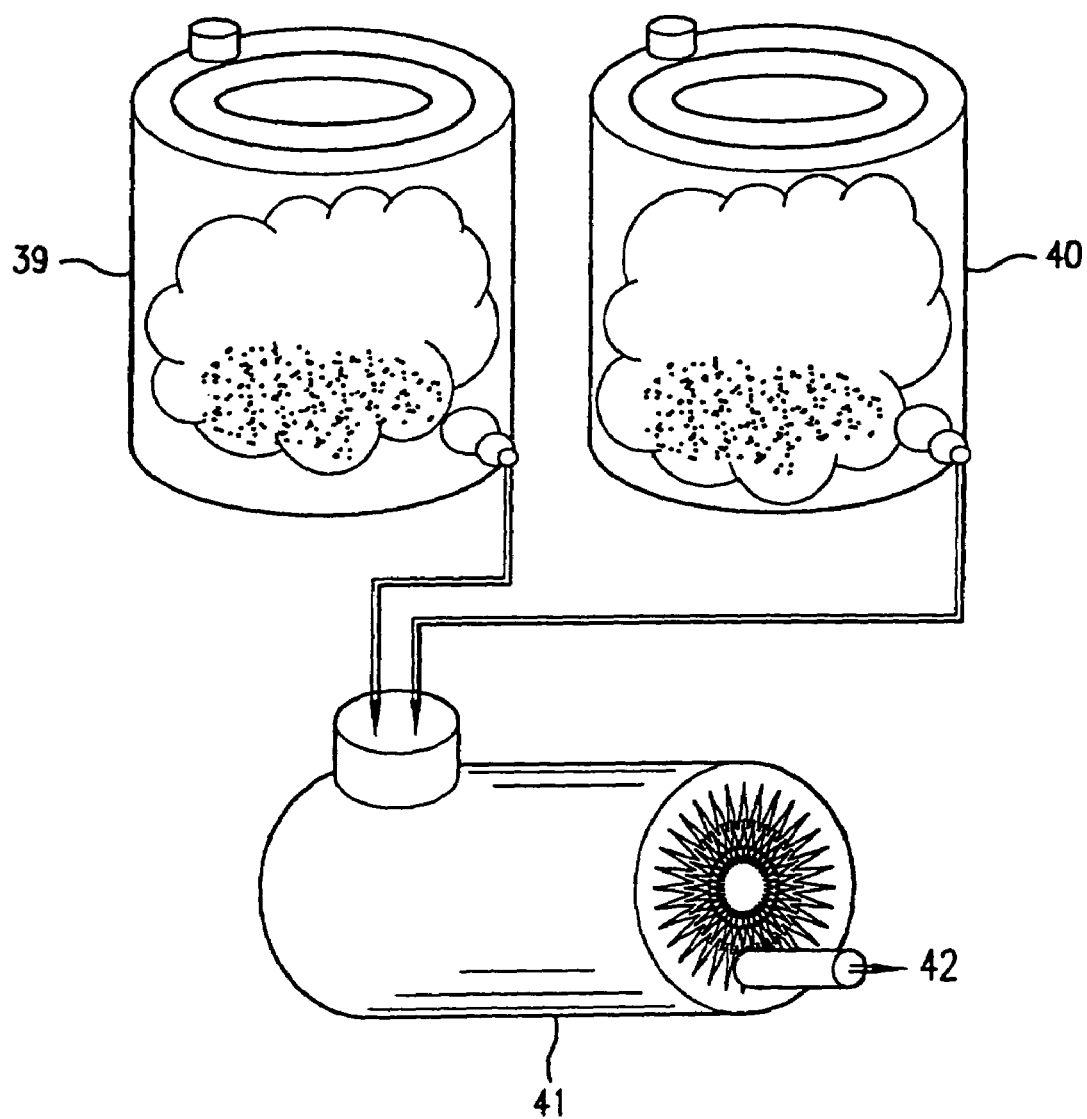

FIG. 9. Fertilizer production process. 39 mixture of yeasts; 40 mixture of organic and inorganic materials; 41 granulizer; 42 fertilizer granules.

Figure 10:
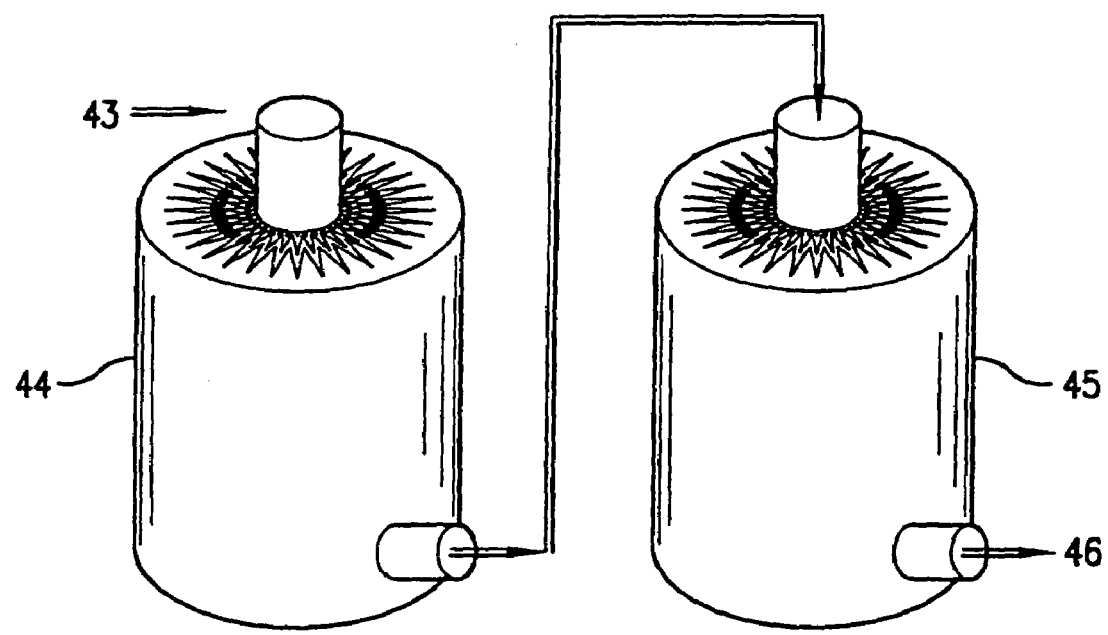

FIG. 10. Drying process. 43 fertilizer granules; 44 first dryer; 45 second dryer; 46 dried fertilizer.

Figure 11:
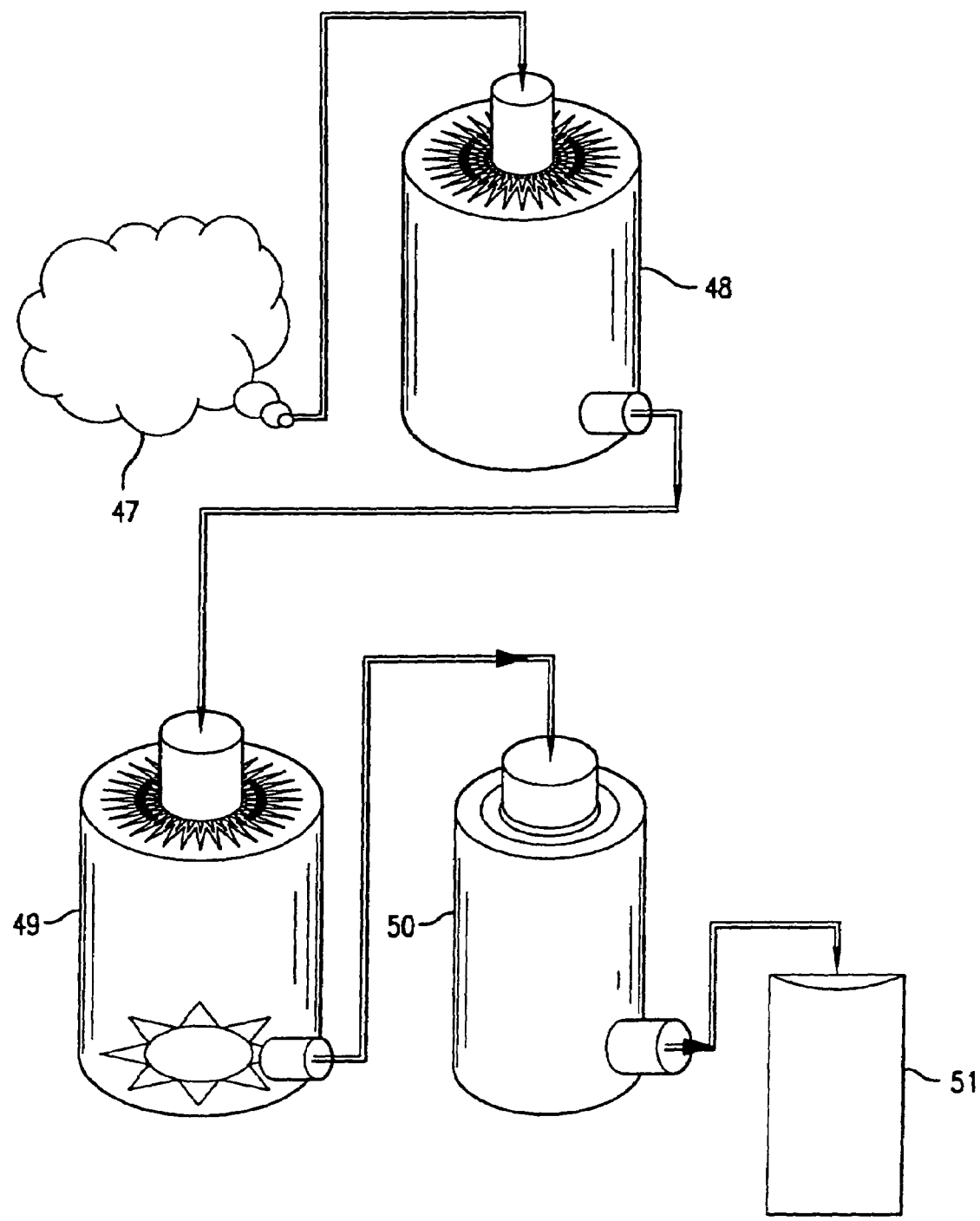

FIG. 11. Cooling and packaging process. 47 dried fertilizer; 48 cooler; 49 separator; 50 bulk bag filler; 51 final product.

5. DETAILED DESCRIPTION OF THE INVENTION

The present invention provides biological fertilizer compositions that comprise yeast cells and poultry manure. The present invention also provides methods for manufacturing the biological fertilizer compositions as well as methods for using the biological fertilizer compositions.

The biological fertilizer compositions of the invention can replace chemical/mineral fertilizers in supplying nitrogen (N), phosphorus (P), and potassium (K) to plants, especially crop plants. The inclusion of poultry manure in the biological fertilizer compositions of the invention provide an environmentally acceptable and economic method for recycling poultry manure.

According to the invention, the biological fertilizer compositions comprise poultry manure and a plurality of yeast cell components. Each yeast cell component is a population of yeast cells which comprises a plurality of yeast cells that are capable of performing a desired function. The yeast cell components of the invention can provide the following six basic functions: (1) fixation of atmospheric nitrogen; (2) decomposition of phosphorus minerals or compounds, or maintaining a balance of phosphorus compounds; (3) decomposition of potassium minerals or compounds; (4) decomposition of complex or high molecular weight carbon materials or compounds; (5) overproduction of growth factors; and (6) overproduction of ATP. The yeast cell components of the invention can provide the following supplementary functions: (7) suppression of growth of pathogens, (8) degradation of undesirable chemicals, or (9) reducing the odor of organic materials.

In one embodiment, a biological fertilizer composition of the invention comprises (I) poultry manure; (II) at least one of the following yeast cell component: (a) a first yeast cell component comprising a first plurality of yeast cells that fix nitrogen; (b) a second yeast cell component comprising a second plurality of yeast cells that decompose phosphorus compounds; or (c) a third yeast cell component comprising a third plurality of yeast cells that decompose potassium compounds; and (III) at least one of the following: (d) a fourth yeast cell component comprising a fourth plurality of yeast cells that suppress the growth of pathogenic microorganisms; (e) a fifth yeast cell component comprising a fifth plurality of yeast cells that degrade antibiotics; or (f) a sixth yeast cell component comprising a sixth plurality of yeast cells that reduce the odor of the biological fertilizer composition. Thus, a biological fertilizer composition of the invention comprises at least two yeast cell components, one providing one of the three listed basic functions and one providing a supplementary function. In another embodiment, the biological fertilizer composition as described above further comprises at least one of the following: (g) a seventh yeast cell component comprising a seventh plurality of yeast cells that convert complex carbon compounds to simple carbohydrates; (h) an eighth yeast cell component comprising an eighth plurality of yeast cells that overproduce growth factors; or (i) a ninth yeast cell component comprising a ninth plurality of yeast cells that overproduce adenosine triphosphate. In preferred embodiments, the biological fertilizer compositions of the invention comprises yeast cell components that provide all six basic functions, plus at least one of the supplementary functions. Thus, the preferred biological fertilizer compositions comprise seven, eight or nine different yeast cell components.

The pluralities of the yeast cells of the invention can be added to poultry manure or existing organic fertilizers to improve their performance.

The poultry manure in the fertilizer compositions provides a source of nitrogen, phosphorus and potassium. Optionally, the fertilizer compositions may include an inorganic component comprising minerals which provides an additional source of phosphorous and/or potassium, and other minerals such as but not limited to calcium, magnesium, and sulfur; and micronutrients, such as but not limited to boron, copper, iron, manganese, molybdenum, and zinc.

The biological fertilizer compositions of the present invention have many advantages over mineral fertilizers and organic fertilizers. Because the biological fertilizer of the present invention utilize metabolic activities of living yeasts to convert raw materials, such as atmospheric nitrogen, and phosphorus and potassium compounds in the substrate component, into plant nutrients, the conversion and release of such nutrients by the yeast cells is regulated in part by the nutrient content of the soil. The nutrient content of the soil in turn depends in part on both the environment and the changing needs of plants. Therefore, the release of plant nutrients by the biological fertilizer compositions is adaptable to the soil condition and can be sustained over a period of time.

In addition to supplying nutrients to plants, the biological fertilizer compositions of the invention provide up to three supplementary functions that mitigate some of the undesirable properties of poultry manure that tend to restrict their use as organic fertilizers. The presence of pathogenic bacteria in poultry manure poses a health risk to humans and livestock. The biological fertilizer compositions can include a component of yeast cells that can suppress the proliferation of pathogenic bacteria, thereby reducing the risk of infection, and circumventing the need to use chemicals in controlling the spread of such pathogens. Another yeast cell component that can be included in the composition is capable of reducing the odor of poultry manure, thus making its inclusion in a fertilizer more acceptable. Yet another yeast cell component can be included to degrade undesirable chemicals, such as antibiotic feed additives, which are found in poultry manure. These supplementary functions generally lessen the adverse impact on the environment of using poultry manure in a fertilizer. The yeast cell components that provide the supplementary functions can each be separately included with the other six yeast cell components that provide the basic functions, or in combination with each other and the other six components to provide the desired assortment of supplementary functions.

While the following terms are believed to have well-defined meanings in the art, the following are set forth to facilitate explanation of the invention.

As used herein, the term "nitrogen fixation" or "fixation of atmospheric nitrogen" encompasses biological processes in which molecular nitrogen or nitrogen in the atmosphere is converted into one or more nitrogenous (N) compounds, including but not limited to, ammonia, ammonium salts, urea, nitrites, and nitrates.

As used herein, the phrase "decomposition of phosphorus minerals or compounds" refers to biological processes which convert phosphorus (P) compounds, such as but not limited to those water-insoluble phosphorus compounds present in minerals, such as phosphate rock, into one or more different phosphorus compound(s) which are biologically available or more readily assimilable, i.e., usable for survival and/or growth, by plants and other yeasts. For example, the resulting phosphorus compounds may be more soluble in water or weak acid, and can thus be taken up by the roots of plants. Non-limiting examples of biologically available or assimilable phosphorus compounds include various classes of phosphates such as $H_3PO_4$, $H_2PO_4^-$ and $HPO_4^{2-}$.

As used herein, the phrase "maintenance of a balance of phosphorus compounds" refers to biological processes which convert biologically unavailable or water-insoluble phosphorus compounds into one or more different phosphorus compound(s) which are more biologically available or soluble in water, wherein the processes are sensitive to excess or the lack of phosphorus (P) compounds in the local environment. The conversion process is downregulated when the level of P compound is high (i.e., greater than about 180 ppm) and upregulated when level of P compound is low (i.e., greater than about 60 ppm)

As used herein, the phrase "decomposition of potassium minerals or compounds" refers to biological processes which convert potassium (K) compounds, such as but not limited to those water-insoluble potassium compounds present in potassium-containing minerals and materials, into one or more different potassium compound(s) which can be biologically available or more readily assimilable by plants and other yeasts. For example, the resulting potassium compounds may be more soluble in water, and can thus be taken up by the roots of plants.

As used herein, the phrase "decomposition of complex or high molecular weight carbon minerals, materials or compounds" refers to the biological conversion of a complex organic or inorganic carbon molecule (e.g. complex carbohydrates like cellulose and lignin) into one or more carbon compound(s) which are of a lower molecular weight (e.g., simple carbohydrates) and which can be readily used for survival and/or growth by plants and yeasts. This process includes those reactions where long chains of carbon atoms in a polymeric carbon compound are cleaved.

As used herein, the term "growth factors" refers to molecules commonly required for the growth of yeasts, including but not limited to vitamins, in particular, vitamin B complexes, e.g., vitamin B-1, riboflavin (vitamin B-2), vitamin B-12, niacin (B-3), pyridoxine (B-6), pantothenic acid (B-5); folic acid; biotin; para-aminobenzoic acid; choline; and inositol.

For the purpose of this invention, the above-described five functions together with the overproduction of growth factors and ATP are referred to as the basic functions.

As used herein, the phrase "suppressing the growth of pathogens" refers to a decrease or lack of increase in the number of pathogenic microorganisms present in a sample of poultry manure over a period of time, as a result of the presence of the yeast cells of the invention in the sample. It is to be understood that in the absence of the yeast cells, the number of pathogens in the sample would increase naturally. Many such microorganisms cause diseases in humans and animals, and may include bacteria such as *Escherichia* species, *Salmonella* species, *Shigella* species, *Mycobacterium* species, *Staphylococcus* species, *Bacillus* species, *Streptococcus* and *Diplococcus* species.

As used herein, the phrase "degradation of undesirable chemicals" refers to biological or biochemical processes which result in the conversion of chemical compounds that are undesirable in a fertilizer to an inactive form, such as the breakdown of such compounds into lower molecular weight compounds. Antibiotics are commonly present in organic materials and such compounds are not desired in a fertilizer because of the potential risk of ingestion by humans, for example, by eating vegetables grown using a fertilizer comprising contaminated organic material, and the possible spread of antibiotic resistance in the environment. Many antibiotics are added to animal feed to protect various farm animals, such as chicken, turkey, and swine, from bacterial and parasitic diseases, and to promote growth. A significant amount of antibiotic feed additive is excreted by the animals, and thus accumulates in manure and sludge. Many kinds of antibiotics have been used in animal operations, such as but not limited to aminoglycosides, tetracyclines, beta-lactams, glycopeptides, and macrolides. Examples of antibiotics approved for use in farms in United States include but are not limited to, bacitracin methylene disalicylate, bacitracin zinc, bambermycins, oxytetracycline, chlortetracycline, penicillin, tylosin/sulfamethazine, roxarsone, nitrasone, monensin, lasalocid, carbodox, tiamulin, hygromycin B, nystatin, novobiocin, sulfadimethoxine, ormetroprim, lincomycin, fenbendazole, and virginiamycin. The presence and quantity of such antibiotics in a composition can be determined by any methods known in the art, for example, high performance liquid chromatography (HPLC).

As used herein, the phrase "reducing the odor of organic materials" refers to a process which results in a lower concentration of one or more odorous compounds in poultry manure. Odorous compounds, such as but not limited to hydrogen sulfide, ammonia, indole, skatole (i.e, 3-methyl-1H-indole), p-cresol, and organic acids, are known to contribute to the malodorous quality of manure. The concentration of such malodorous compounds in poultry manure or in a sample of air in contact with the manure can be determined by any method well known in the art, including but not limited to gas chromatography. Odor is a perception of smell by an organism with olfactory organs. A reduction of the intensity of the odor associated with poultry manure can be determined subjectively. Various methods and techniques are known to measure the intensity of an odor. One subjective measurement of odor intensity is to measure the dilution necessary so that the odor is imperceptible or doubtful to a human or animal test panel. Alternatively, a recognition threshold may also be used which is a higher concentration at which the character of the odor is recognized. Any methods and techniques for objectively or subjectively determine the intensity of an odor can be used to monitor the performance of the compositions and methods of the invention.

For the purpose of this invention, the suppression of growth of pathogens, degradation of undesirable chemicals, and reduction of odor of organic materials are referred to as the supplementary functions or activities.

The inventor discovered that, under various culture conditions, yeasts can be induced to exhibit seven different basic functions and three supplementary functions. The culture condition determines the activity which is activated or enhanced in the cultured yeasts. The specific culture conditions for each of the ten functions are described in details in sections 5.1 to 5.10 respectively.

According to the invention, a yeast cell component of the biological fertilizer composition is produced by culturing a plurality of yeast cells in an appropriate culture medium in the presence of an alternating electromagnetic field or multiple alternating electromagnetic fields in series over a period of time. The culturing process allows yeast spores to germinate, yeast cells to grow and divide, and can be performed as a batch process or a continuous process. As used herein, the terms "alternating electromagnetic field", "electromagentic field" or "EM field" are synonymous. An electromagnetic field useful in the invention can be generated by various means well known in the art. A schematic illustration of exemplary setups are depicted respectively in FIG. 1. An electromagnetic field of a desired frequency and a desired field strength is generated by an electromagnetic wave source (3) which comprises one or more signal generators that are capable of generating electromagnetic waves, preferably sinusoidal waves, and preferably in the frequency range of 30 MHz-3000 MHz. Such signal generators are well known in the art. Signal generators capable of generating signal with a narrower frequency range can also be used. If desirable, a signal amplifier can also be used to increase the output signal, and thus the field strength.

The electromagnetic field can be applied to the culture by a variety of means including placing the yeast cells in close proximity to a signal emitter connected to a source of electromagnetic waves. In one embodiment, the electromagnetic field is applied by signal emitters in the form of electrodes that are submerged in a culture of yeast cells (1). In a preferred embodiment, one of the electrodes is a metal plate, and the other electrode comprises a plurality of wires configured inside the container (2) so that the energy of the electromagnetic field can be evenly distributed in the culture. The number of electrode wires used depends on both the volume of the culture and the diameter of the wire. For example, for a culture having a volume of 5000 ml, one electrode wire having a diameter of between 0.1 to 1.2 mm can be used for each 100 ml of culture; for a culture having a volume greater than 1000 l, one electrode wire having a diameter of between 3 to 30 mm can be used for each 1000 l of culture.

In preferred embodiments, yeasts of the genera of *Saccharomyces, Schizosaccharomyces, Sporobolomyces, Torulopsis, Trichosporon, Wickerhamia, Ashbya, Blastomyces, Candida, Citeromyces, Crebrothecium, Cryptococcus, Debaryomyces, Endomycopsis; Geotrichum, Hansenula, Kloeckera, Lipomyces, Pichia, Rhodosporidium,* and *Rhodotorula* can be used in the invention.

Non-limiting examples of yeast strains include *Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.14, AS2.16, AS2.56, AS2.69, AS2.70, AS2.93, AS2.98, AS2.101, AS2.109, AS2.110, AS2.112, AS2.139, AS2.173, AS2.174, AS2.182, AS2.196, AS2.242, AS2.336, AS2.346, AS2.369, AS2.374, AS2.375, AS2.379, AS2.380, AS2.382, AS2.390, AS2.393, AS2.395, AS2.396, AS2.397, AS2.398, AS2.399, AS2.400, AS2.406, AS2.408, AS2.409, AS2.413, AS2.414, AS2.415, AS2.416, AS2.422, AS2.423, AS2.430, AS2.431, AS2.432, AS2.451, AS2.452, AS2.453, AS2.458, AS2.460, AS2.463, AS2.467, AS2.486, AS2.501, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI 1001, IFFI 1002, IFFI 1005, IFFI 1006, IFFI 1008, IFFI 1009, IFFI 1010, IFFI 1012, IFFI 1021, IFFI 1027, IFFI 1037, IFFI 1042, IFFI 1043, IFFI 1045, IFFI 1048, IFFI 1049, IFFI 1050, IFFI 1052, IFFI 1059, IFFI 1060, IFFI 1063, IFFI 1202, IFFI 1203, IFFI 1206, IFFI 1209, IFFI 1210, IFFI 1211, IFFI 1212, IFFI 1213, IFFI 1215, IFFI 1220, IFFI 1221, IFFI 1224, IFFI 1247, IFFI 1248, IFFI 1251, IFFI 1270, IFFI 1277, IFFI 1287, IFFI 1289, IFFI 1290, IFFI 1291, IFFI 1292, IFFI 1293, IFFI 1297, IFFI 1300, IFFI 1301, IFFI 1302, IFFI 1307, IFFI 1308, IFFI 1309, IFFI 1310, IFFI 1311, IFFI 1331, IFFI 1335, IFFI 1336, IFFI 1337, IFFI 1338, IFFI 1339, IFFI 1340, IFFI 1345, IFFI 1348, IFFI 1396, IFFI 1397, IFFI 1399, IFFI 1411, IFFI 1413; *Saccharomyces cerevisiae* Hansen Var. ellipsoideus (Hansen) Dekker, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces chevalieri* Guillermond, AS2.131, AS2.213; *Saccharomyces delbrueckii*, AS2.285; *Saccharomyces delbrueckii* Lindner var. mongolicus Lodder et van Rij, AS2.209, AS2.1157; *Saccharomyces exiguus* Hansen, AS2.349, AS2.1158; *Saccharomyces fermentati* (Saito) Lodder et van Rij, AS2.286, AS2.343; *Saccharomyces logos* van laer et Denamur ex Jorgensen, AS2.156, AS2.327, AS2.335; *Saccharomyces mellis* Lodder et Kreger Van Rij, AS2.195; *Saccharomyces microellipsoides* Osterwalder, AS2.699; *Saccharomyces oviformis* Osterwalder, AS2.100; *Saccharomyces rosei* (Guilliermond) Lodder et kreger van Rij, AS2.287; *Saccharomyces rouxii* Boutroux, AS2.178, AS2.180, AS2.370, AS2.371; *Saccharomyces sake* Yabe, ACCC2045; *Candida arborea*, AS2.566; *Candida Krusei* (Castellani) Berkhout, AS2.1045; *Candida lambica* (Lindner et Genoud) van. Uden et Buckley, AS2.1182; *Candida lipolytica* (Harrison) Diddens et Lodder, AS2.1207, AS2.1216, AS2.1220, AS2.1379, AS2.1398, AS2.1399, AS2.1400; *Candida parapsilosis* (Ashford) Langeron et Talice, AS2.590; *Candida parapsilosis* (Ashford) et Talice Var. intermedia Van Rij et Verona, AS2.491; *Candida pulcherriman* (Lindner) Windisch, AS2.492; *Candida rugousa* (Anderson) Diddens et Loddeer, AS2.511, AS2.1367, AS2.1369, AS2.1372, AS2.1373, AS2.1377, AS2.1378, AS2.1384; *Candida tropicalis* (Castellani) Berkout, ACCC2004, ACCC2005, ACCC2006, AS2.164, AS2.402, AS2.564, AS2.565, AS2.567, AS2.568, AS2.617, AS2.1387; *Candida utilis* Henneberg Lodder et Kreger Van Rij, AS2.120, AS2.281, AS2.1180; *Crebrothecium ashbyii* (Guillermond) Routein, AS2.481, AS2.482, AS2.1197; *Geotrichum candidum* Link, ACCC2016, AS2.361, AS2.498, AS2.616, AS2.1035, AS2.1062, AS2.1080, AS2.1132, AS2.1175, AS2.1183; *Hansenula anomala* (Hansen) H et P sydow, ACCC2018, AS2.294, AS2.295, AS2.296, AS2.297, AS2.298, AS2.299, AS2.300, AS2.302, AS2.338, AS2.339, AS2.340, AS2.341, AS2.470, AS2.592, AS2.641, AS2.642, AS2.635, AS2.782, AS2.794; *Hansenula arabitolgens* Fang, AS2.887; *Hansenula jadinii* Wickerham, ACCC2019; *Hansenula saturnus* (Klocker) H et P sydow, ACCC2020; *Hansenula schneggii* (Weber) Dekker, AS2.304; *Hansenula subpelliculosa* Bedford, AS2.738, AS2.740, AS2.760, AS2.761, AS2.770, AS2.783, AS2.790, AS2.798, AS2.866; *Kloeckera apiculata* (Reess emend. Kilocker) Janke, ACCC2021, ACCC2022, ACCC2023, AS2.197, AS2.496, AS2.711, AS2.714; *Lipomyces starkeyi* Lodder et van Rij, ACCC2024, AS2.1390; *Pichia farinosa* (Lindner) Hansen, ACCC2025, ACCC2026, AS2.86, AS2.87, AS2.705, AS2.803; *Pichia membranaefaciens* Hansen, ACCC2027, AS2.89, AS2.661, AS2.1039; *Rhodosporidium toruloides* Banno, ACCC2028; *Rhodotorula glutinis* (Fresenius) Harrison, ACCC2029, AS2.280, ACCC2030, AS2.102, AS2.107, AS2.278, AS2.499, AS2.694, AS2.703, AS2.704, AS2.1146; *Rhodotorula minuta* (Saito) Harrison, AS2.277; *Rhodotorula rubar* (Demme) Lodder, ACCC2031, AS2.21, AS2.22, AS2.103, AS2.105, AS2.108, AS2.140, AS2.166, AS2.167, AS2.272, AS2.279, AS2.282; *Saccharomyces carlsbergensis* Hansen, ACCC2032, ACCC2033, AS2.113, AS2.116, AS2.118, AS2.121, AS2.132, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042; *Saccharomyces uvarum* Beijer, IFFI 1023, IFFI 1032, IFFI 1036, IFFI 1044, IFFI 1072, IFFI 1205, IFFI 1207; *Saccharomyces willianus* Saccardo, AS2.5, AS2.7, AS2.119, AS2.152, AS2.293, AS2.381, AS2.392, AS2.434, AS2.614, AS2.1189; *Saccharomyces* sp., AS2.311; *Saccharomyces ludwigii* Hansen, ACCC2044, AS2.243, AS2.508; *Saccharomyces sinenses* Yue, AS2.1395; *Schizosaccharomyces octosporus* Beijerinck, ACCC 2046, AS2.1148; *Schizosaccharomyces pombe* Linder, ACCC2047, ACCC2048, AS2.248, AS2.249, AS2.255, AS2.257, AS2.259, AS2.260, AS2.274, AS2.994, AS2.1043, AS2.1149, AS2.1178, IFFI 1056; *Sporobolomyces roseus* Kluyver et van Niel, ACCC 2049, ACCC 2050, AS2.619, AS2.962, AS2.1036, ACCC2051, AS2.261, AS2.262; *Torulopsis candida* (Saito) Lodder, ACCC2052, AS2.270; *Torulopsis famta* (Harrison) Lodder et van Rij, ACCC2053, AS2.685; *Torulopsis globosa* (Olson et Hammer) Lodder et van Rij, ACCC2054, AS2.202; *Torulopsis inconspicua* Lodder et van Rij, AS2.75; *Trichosporon behrendii* Lodder et Kreger van Rij, ACCC2055, AS2.1193; *Trichosporon capitatum* Diddens et Lodder, ACCC2056, AS2.1385; *Trichosporon cutaneum* (de Beurm et al.) Ota, ACCC2057, AS2.25, AS2.570, AS2.571, AS2.1374; *Wickerhamia fluoresens* (Soneda) Soneda, ACCC2058, AS2.1388.

Certain yeast species that can be activated or induced according to the present invention and are included in the present invention are known to be pathogenic to human and/or other living organisms, for example, *Ashbya gossypii; Blastomyces dermatitidis; Candida albicans; Candida parakrusei; Candida tropicalis; Citeromyces matritensis; Crebrothecium ashbyii; Cryptococcus laurentii; Cryptococcua neoformans; Debaryomyces hansenii; Debaryomyces kloeckeri; Debaryomyces* sp.; *Endomycopsis fibuligera*. Under certain circumstances, it may be less preferable to use such pathogenic yeasts in the biological fertilizer of the invention, for example, if such use in an open field may endanger the health of human and/or other living organisms.

Yeasts of the *Saccharomyces* genus are generally preferred. Among strains of *Saccharomyces cerevisiae*, *Saccharomyces cerevisiae* Hansen is a preferred strain. The most preferred strains of yeast are *Saccharomyces cerevisiae* strains having accession numbers AS2.504, AS2.558, AS2.413, AS2.397, AS2.69, AS2.109, AS2.607, AS2.516, AS2.561, AS2.422, AS2.393, AS2.631, AS2.982, AS2.560, AS2.467, AS2.415, AS2.375, AS2.628, AS2.1190, AS2.562, AS2.463, AS2.409, AS2.379, AS2.666, AS2.631, AS2.182, AS2.431, AS2.606, AS2.53, AS2.611, AS2.414, AS2.576, AS2.483, IFFI 1211, IFFI 1293, IFFI 1308, IFFI 1210, IFFI 1213, IFFI 1307, IFFI 1206, IFFI 1052, IFFI 1301, IFFI 1291, IFFI 1202, IFFI 1021, IFFI 1059, IFFI 1052, IFFI 1441, IFFI 1008, IFFI 1220, IFFI 1302, and IFFI 1023 as deposited at the China General Microbiological Culture Collection Center (CGMCC).

Generally, yeast strains useful for the invention can be obtained from private or public laboratory cultures, or publically accessible culture deposits, such as the American Type Culture Collection, 10801 University Boulevard, Manassas, Va. 20110-2209 and the China General Microbiological Culture Collection Center (CGMCC), China Committee for Culture Collection of Microorganisms, Institute of Microbiology, Chinese Academy of Sciences, Haidian, P.O. Box 2714, Beijing, 100080, China.

The following yeast strains are preferred for making the P-balancing yeasts of the invention: AS2.558, AS2.118, AS2.103, AS2.132, AS2.121, AS2.189, AS2.216, AS2.265, AS2.417, AS2.420, AS2.200, AS2.162, AS2.440, AS2.277, AS2.441, AS2.443, AS2.444, AS2.605, AS2.595, AS2.638, AS2.742, AS2.748, AS2.14, AS2.16, AS2.56, AS2.69, AS2.70, AS2.109, AS2.112, AS2.375, AS2560, AS2.561, AS2.562, AS2.559, AS2.501, AS2.502, AS2.503, AS2.504, IFFI1001, IFFI1002, IFFI1005, IFFI1006, IFFI1008, IFFI1009, IFFI1010, IFFI1012, IFFI1021, IFFI1027, IFFI1037, IFFI1042, IFFI1060, IFFI1063, IFFI1202, IFFI1203, IFFI1206, IFFI1209, IFFI1210, IFFI1211, IFFI1212, IFFI1213, IFFI1215, IFFI1220, IFFI1220, IFFI1221, IFFI1224, IFFI1247, IFFI1248, IFFI1251, IFFI1270, IFFI1277, IFFI1287, IFFI1289, IFFI1290, IFFI1291, IFFI1292, IFFI1293, IFFI1297, IFFI1300, IFFI1301, IFFI1307, IFFI1308, IFFI1309, IFFI1310, IFFI1311, IFFI1331, IFFI1335, IFFI1336, IFFI1337, IFFI1338, IFFI1340, IFFI1339, IFFI1345, IFFI1396, IFFI1399, IFFI1411, IFFI1413, IFFI1023, IFFI1032, IFFI1036, IFFI1044, and IFFI1207.

Although it is preferred, the preparation of the yeast cell components of the invention is not limited to starting with a pure strain of yeast. Each yeast cell component may be produced by culturing a mixture of yeast cells of different species or strains. The constituents of a yeast cell component can be determined by standard yeast identification techniques well known in the art.

Some yeasts may perform one of the desired functions more efficiently than others. The table below lists the species and accession numbers of various yeast strains and the preferred functions for which the respective strains are stimulated by the methods of the invention.

The ability and efficiency of any species or strain of yeast to perform any one of the ten desired functions before or after culturing under the conditions of the invention can readily be tested by methods known in the art. For example, the amount of nitrogen fixed can be determined by a modified acetylene reduction method as described in U.S. Pat. No. 5,578,486 which is incorporated herein by reference in its entirety. The modified acetylene reduction method determines the amount of nitrogen fixed by measuring the decrease in molecular nitrogen in a volume of air. The amount of nitrogen fixed can also be determined by measurement of the ammonia and nitrates produced by the yeast cells (see, for example, Grewling et al., 1965, Cornell Agr Exp Sta Bull 960:22-25). A standard method that is applicable to determine total organic nitrogen is the Kjeldahl method.

The amount of phosphorus available to plants as a result of conversion from insoluble or biologically-unavailable phosphorus compounds can be determined by the molybdenum blue method (see, for example, Murphy et al., 1962, Analytica Chimica Acta 27:31-36) or the UV absorption method; whereas the amount of available potassium converted from insoluble or biologically-unavailable potassium compounds can be determined, for example, by flame atomic absorption spectroscopy (see, for example, Puchyr, et al., 1986, J. Assoc. Off. Anal. Chem. 69:868-870). The ability of the yeasts to supply biologically available N, P, and K after the biological fertilizer composition has been added to soil can be tested by many techniques known in the art. For example, plant-available ammonia, nitrates, P, and K produced by the yeast cells in soil can be extracted and quantitatively analyzed by the Morgan soil test system (see, for example, Lunt et al., 1950, Conn Agr Exp Sta Bull 541).

Methods well known in the art can be used for detecting and analyzing various organic molecules in manure and in soil, including HPLC. Similarly, methods well known in the art can be used for detecting and counting the number of viable microorganisms and the total number of microorganisms in a sample.

Without being bound by any theory or mechanism, the inventor believes that the culture conditions activate and/or enhance the expression of a gene or a set of genes in a yeast cell such that the cell becomes active or more efficient in performing certain metabolic activities which lead to the respective desired results.

Poultry manure is used to form the organic substrate component of the biological fertilizer compositions of the invention. The term "poultry manure" as used herein broadly encompasses the feces and urine of domesticated birds, with or without accompanying litter such as straw, hay, or bedding, that is traditionally used to fertilize land. Poultry manure includes but are not limited to manure produced by chicken, duck, turkey, goose, quail, squab, ostrich, and the like. Poultry manure include excrement or guano produced by non-domesticated bird species. Typically, poultry manure is produced by birds used in animal operations such as but not limited to ranches, farms, slaughterhouses, and markets.

Optionally, an inorganic substrate component can be included in the biological fertilizer compositions of the invention. The inorganic substrate component can include but not limited to phosphate rock or rock phosphate, apatite, phosphorite, sylvinite, halite, carnalitite, and potassium mica.

Due to the variation of constituents in poultry manure, it may be desirable to subject a sample of a batch of poultry manure to analysis to determine the amount of plant nutrient present. Methods of soil analysis well known in the art can be used to measure the amount of N, P, K, calcium, magnesium, zinc, iron, manganese, copper, sodium and sulfur in the manure.

In various embodiments, the biological fertilizer compositions of the present invention each comprises at least seven yeast cell components capable of performing six basic functions plus at least one of the supplementary functions. In a most preferred embodiment, the biological fertilizer compositions comprise nine yeast cell components, in which case the six basic functions and all three supplementary functions are provided. It will be understood that alternative formulations are also contemplated.

In one particular embodiment of the invention, when a batch of poultry manure that is relatively rich in biologically-available phosphorus is used, the biological fertilizer composition can be formulated to comprise yeast cells that can maintain a balance of phosphorus compounds instead of yeast cells that decompose phosphorus-containing minerals or compounds. Moreover, if desired, the biological fertilizer composition may comprise lesser quantities of one or more of the above-described yeast cell components that supply one of the six basic functions. For example, if the biological fertilizer composition is to be used in soil that is rich in potassium, the biological fertilizer composition can be formulated to comprise lesser amount of the yeast cells that can decompose potassium-containing minerals or compounds.

In another embodiment of the invention, where the yeast cells of the various yeast cell components are present in a mixture, the yeast cells can be cultured under certain conditions such that the yeast cells with different functions can supply each other with and/or rely on each other for nutrients and growth factors. As a result, a symbiosis-like relationship is established among the various yeast cell components in the fertilizer compositions of the invention. This culturing process is optional but can improve the stability and efficiency of the compositions such that the resulting fertilizer is made more suitable for long term use in natural soil environments. The culturing conditions for this optional process are described in Section 5.11.

In yet another embodiment of the invention, the yeast cells may also be cultured under certain conditions so as to adapt the yeast cells to a particular type of soil. This culturing process is optional, and can be applied to each yeast cell component separately or to a mixture of yeast cell components. The result is better growth and survival of the yeast cells in a particular soil environment. The culturing conditions for this optional process are described in Section 5.12.

As used herein, the biological fertilizer composition supports or enhances plant growth, if in the presence of the biological fertilizer in the soil, or applied to the roots, stems, leaves or other parts of the plant, the plant or a part of the plant gains viability, size, weight, rate of germination, rate of growth, or rate of maturation. Thus, the biological fertilizer compositions have utility in any kind of agricultural, horticultural, and forestry practices. The biological fertilizer compositions can be used for large scale commercial farming, in open fields or in greenhouse, or even in interiors for decorative plants. Preferably, the biological fertilizer is used to enhance the growth of crop plants, such as but not limited to cereal crops, vegetable crops, fruit crops, flower crops, and grass crops. For example, the biological fertilizer compositions may be used with wheat, barley, corn, soybean, rice, oat, potato, apple, orange, tomato, melon, cherry, lemon, lettuce, carrot, sugar cane, tobacco, cotton, etc.

The biological fertilizer compositions of the invention may be applied in the same manner as conventional fertilizers. As known to those skilled in the relevant art, many methods and appliances may be used. In one embodiment, a mixture of culture broths of the east strains of the present invention and poultry manure are applied directly to soil or plants. In another embodiment, dried powders of the yeast strains of the present invention and poultry manure are applied to soil or plants. The biological fertilizer compositions may be applied to soil, by spreaders, sprayers, and other mechanized means which may be automated. The biological fertilizer compositions may be applied directly to plants, for example, by soaking seeds and/or roots, or spraying onto leaves. Such application may be made periodically, such as once per year, or per growing season, or more frequently as desired. Although not necessary in most cases, the biological fertilizer compositions of the invention can also be used in conjunction or in rotation with other types of fertilizers.

In one preferred embodiment, the biological fertilizer composition of the invention, i.e., yeasts of the invention mixed with poultry manure in granular form, is used as a basal fertilizer which is applied into the soil at the depth of the major root system of the crop. Prior to application, the ground should be loosened and clear of weeds. The biological fertilizer composition can be spread evenly onto the ground, added to holes or long furrows in the ground. For existing fruit trees, a circular furrow of about 5 to 30 cm deep is dug into which the biological fertilizer composition of the invention is added. The ground, holes, or furrows containing the biological fertilizer composition can then be covered with soil and watered throughly. After 3 to 7 days, the area is ready for planting or sowing. For rice, the ground is flooded with water for 3 to 7 days before planting the seedlings. If used in sandy soil with a shallow root system, a depth of 5 to 15 cm is used; with a deep root system, 5 to 25 cm is recommended. In clay soil with a shallow root system, a depth of 2 to 10 cm is used; with a deep root system, 2 to 15 cm is recommended. The desired effect is that the biological fertilizer composition is contact with or in very close proximity to the roots of the plants. Preferably, after application of the fertilizer and/or planting, the soil is not disturbed. Generally, the operation temperature of the fertilizer is between 5° C. to 45° C., optimally between 16° C. to 30° C.; the preferred pH range is between 5.5 to 8.5, and optimally between 6.5 to 7.5.

| Recommended Dosage | |
| --- | --- |
| Crop | Amount of Biological Fertilizer |
| Vegetables (short-growing) | 600-900 kg/ha |
| Vegetable (long-growing) | 900-1200 kg/ha |
| Ground vegetable | 900-1350 kg/ha |
| Solanaceous fruit | 900-1350 kg/ha |
| Root & Tuber vegetable | 750-900 kg/ha |
| Bulb vegetable | 900-1200 kg/ha |
| Legume | 600-1050 kg/ha |
| Fruit Trees | 2-5 kg/tree |
| Paddy Rice | 600-900 kg/ha |
| Wheat & Corn | 750-1200 kg/ha |
| Cotton & Peanut | 600-1200 kg/ha |

Described respectively in Sections 5.1-5.10 are the yeast cell components used for nitrogen fixation, phosphorus compound decomposition, potassium compound decomposition, complex carbon compound decomposition, growth factors production, ATP production, pathogen suppression, degradation of undesirable chemicals, and reduction of odor. Methods for preparing each yeast cell components are described. Section 5.11 describes the methods for establishing a symbiosis-like relationship among yeast strains in a fertilizer composition of the invention. Section 5.12 describes methods for adapting yeast cells of the invention to a particular type of soil. Section 5.13 describes the manufacture of the biological fertilizer compositions of the invention. Methods for the preparation of organic substrates and for the manufacture of the biological fertilizer, including mixing, drying, cooling, and packing, are also described. In various embodiments of the invention, standard techniques for handling, transferring, and storing yeasts are used. Although it is not necessary, sterile conditions or clean environments are desirable when carrying out the processes of the invention.

5.1. Nitrogen-Fixing Yeast Cell Component

Nitrogen fixation is a process whereby atmospheric nitrogen is converted into ammonia and nitrates. Close to 800 species of naturally occurring microorganisms, mostly bacteria and cyanobacteria, from more than 70 genera have been found to be able to fix nitrogen. Some of the nitrogen-fixing microorganisms, such as *Rhizoboum*, form symbiotic association with plants, especially in the root of legumes. Others, such as *Azotobacter*, are free-living and capable of fixing nitrogen in soil.

In the present invention, the ability of a yeast to fix nitrogen is activated or enhanced, and the resulting nitrogen-fixing yeast cells can be used as a component of the biological fertilizer compositions of the invention.

According to the invention, yeast cells that have an enhanced ability to fix nitrogen are prepared by culturing the cells in the presence of an electromagnetic field in an appropriate culture medium. The frequency of the electromagnetic field for activating or enhancing nitrogen fixation in yeasts can generally be found within the range of 800 MHz-1000 MHz. After the yeast cells have been cultured for a sufficient period of time, the cells can be tested for their ability to fix nitrogen by methods well known in the art.

The method of the invention for making the nitrogen-fixing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1%. These carbon sources can be used individually, or several such carbon sources may be combined in the medium.

Among the inorganic salts which can be incorporated in the culture media are the customary salts capable of yielding sodium, potassium, calcium, phosphate, sulfate, carbonate, and like ions. Non-limiting examples of nutrient inorganic salts are $CaCO_3$, $KH_2PO_4$, $MgSO_4$, $NaCl$, and $CaSO_4$.

TABLE 1

Composition for a culture medium for nitrogen-fixing yeast

| Medium Composition | Quantity |
|---|---|
| $KH_2PO_4$ | 0.2 g |
| $K_2HPO_4$ | 0.2 g |
| $MgSO_4 \cdot 7H_2O$ | 0.25 g |
| $CaCO_3 \cdot 5H_2O$ | 3.5 g |
| $CaSO_4 \cdot 2H_2O$ | 0.5 g |
| NaCl | 0.25 g |
| Yeast extract paste | 0.3 g |
| Sucrose | 12.0 g |
| Distilled water or autoclaved water | 1000 ml |

It should be noted that the composition of the media provided in Table 1 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 800 to about 1000 MHz, preferably in the range of 840.000 to 916.000 MHz. For example and without being limited by such examples, each EM field can have a frequency at about 840, 845, 850, 855, 860, 865, 870, 875, 880, 885, 890, 895, 900, 905, 910, 915, or 920 MHz. The field strength of the EM field(s) is in the range of 10 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 140-280 hours.

For example, using an exemplary apparatus as depicted in FIG. 1, an initial EM field in the range of 10-20 mV/cm, usually at about 12.5 mV/cm is used. After this first period of culture, the yeast cells are further incubated under substantially the same conditions for another period, except that the EM field strength is increased to a higher level in the range of 50-200 mV/cm, usually to about 125 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the nitrogen-fixing yeast cells may be recovered from the culture by various methods known in the art, and stored at a temperature below about 0° C. to 4° C. The nitrogen-fixing yeast cells may also be dried and stored in powder form.

Any methods known in the art can be used to test the activated yeast cells for their ability to fix nitrogen. For example, a modified acetylene reduction method for measuring nitrogen fixed by microorganisms is used to evaluate the nitrogen-fixing capability of the prepared yeast. The modified acetylene reduction method is described in U.S. Pat. No. 5,578,486 which is incorporated herein by reference in its entirety. An alternative method based on 15-N can also be used.

The ability of the yeasts of the invention in fixing nitrogen can be demonstrated by the following two methods:

One ml of activated yeast strain AS2.628 (2-5×10$^7$) was cultured in 1000 ml of Ashby medium at 28° C. in the presence of a series of 8 EM fields in the order stated: 855 MHz at 14 mV/cm for 5 hours; 865 MHz at 14 mV/cm for 5 hours; 875 MHz at 14 mV/cm for 5 hours; 885 MHz at 14 mV/cm for 5 hours; 855 MHz at 120 mV/cm for 30 hours; 865 MHz at 120 mV/cm for 30 hours; 875 MHz at 120 mV/cm for 30 hours; 885 MHz at 120 mV/cm for 30 hours. In a separate container, as control, 1 ml of non-activated yeast was cultured under the same conditions without the EM fields. After culturing, the 1000 ml of yeast cells are mixed with 3000 g sterilized coal dust powder, and then dried at less than 70° C. until the moisture content is less than 5%. The end product in powder form (0.1 g) was sealed with 10 ml of Ashby medium in a 100 ml culture flask (5 flasks for each were used in the experiment). 10 ml of air was removed from the flasks by a syringe and replaced with 10 ml of acetylene (>99% purity). The culture flasks were incubated at 28° C. for 24-120 hours and the amount of acetylene reduced was measured by gas chromatography. The amount of acetylene reduced after 120 hours was greater than 120 μmol/g of the dried powder. There was no significant reduction of acetylene in the control containing non-activated yeasts.

Alternatively, the isotopic nitrogen dilution method can be used. The end product in powder form (0.1 g of non-activated and 0.1 g of activated yeasts) were cultured separately for 96 hours at 28° C. The amount of nitrogen fixed by each was determined and compared. The amount of nitrogen fixed by activated yeasts was greater than 3.5 mg/g of the dried powder. The control containing non-activated yeasts did not show any significant fixation of nitrogen.

5.2. Phosphorus-Decomposing Yeast Cell Component

The phosphorus compound-decomposing (P-decomposing) yeast of the invention converts insoluble or biologically-unavailable phosphorus-containing substances, such as phosphate rock, into soluble phosphorous compounds so that they become available to plants.

In the present invention, the ability of yeasts to decompose insoluble phosphorus-containing substances is activated or enhanced, and the resulting P-decomposing yeast cells can be used as a component of the biological fertilizer compositions of the invention.

In various embodiments, P-decomposing yeast cells are employed in the compositions of the invention when the level of soluble or biologically-available phosphorous is low in the poultry manure. P-decomposing yeast is less preferred when the biologically-available phosphorous level is high which is common in poultry manure.

According to the invention, yeast cells that are capable of P-decomposing are prepared by culturing the cells in the presence of an electromagnetic field in an appropriate culture medium. The frequency of the electromagnetic field for activating or enhancing P-decomposition in microbes can generally be found in the range of 300 MHz to 500 MHz. After the cells have been cultured for a sufficient period of time, the cells can be tested for their ability to decompose phosphorus-containing substances by methods well known in the art.

The method of the invention for making the P-decomposing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1.5%. These carbon sources can be used individually, or several such carbon sources may be combined in the medium.

Among the inorganic salts which can be incorporated in the culture media are the customary salts capable of yielding sodium, potassium, calcium, sulfate, carbonate, and like ions. Non-limiting examples of nutrient inorganic salts are $CaCO_3$, $MgSO_4$, NaCl, and $CaSO_4$. Non-biologically available forms of phosphorus-containing substances in a suitable form are also included in the media as dried organic substrate. Non-limiting examples of dried organic substrate include manure, sludge and garbage of $\geqq 150$ mesh. Other insoluble phosphorus-containing substances can also be used either separately or in combination.

TABLE 2

Composition for a culture medium for P-decomposing yeast

| Medium Composition | Quantity |
|---|---|
| Sucrose | 15 g |
| NaCl | 1.2 g |
| $MgSO_4 \cdot 7H_2O$ | 0.2 g |
| $CaCO_3 \cdot 5H_2O$ | 3.0 g |
| $CaSO_4 \cdot 2H_2O$ | 0.3 g |
| $KNO_3$ | 0.3 g |
| Yeast extract paste | 0.5 g |
| Dried poultry manure | 1.2 g to 2.4 g; Powder of >150 mesh |
| Autoclaved water | 1000 ml |

It should be noted that the composition of the media provided in Table 2 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 300 to about 500 MHz, preferably in the range of 340.000 to 435.000 MHz. For example and without being limited by such examples, each EM field can have a frequency at about 340, 345, 350, 355, 360, 365, 370, 375, 375, 380, 385, 390, 395, 400, 405, 410, 415, 420, 425, 430 or 435 MHz. The field strength of the EM field(s) is in the range of 10 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 140-280 hours.

For example, using an exemplary apparatus as depicted in FIG. 1, an initial field strength in the range of 10-20 mV/cm, usually at about 12.5 mV/cm is used. After this first period of culture, the yeast cells are further incubated under substantially the same conditions for another period, except that the EM field strength is increased to a higher level in the range of 50-200 mV/cm, usually to about 125 mV. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the P-decomposing yeast cells may be recovered from the culture by various methods known in the art, and stored at a temperature below about 0° C. to 4° C. The P-decomposing yeast cells may also be dried and stored in powder form.

The amount of biologically available phosphorus, such as $H_3PO_4$, $H_2PO_4^-$, and $HPO_4^{2-}$, in the culture can be determined by any methods known in the art, including but not limited to UV absorption spectroscopy. The increase can be calculated by the difference between the total amount of biologically available phosphorus in a culture with activated yeasts and the amount of biologically available phosphorus in the same medium with non-activated yeast. For example, 1 ml of *Saccharomyces cerevisiae* strain AS2.399 (2 to 5×10$^7$ yeasts/ml) is inoculated into 1000 ml of a medium according to Table 2. The culture is incubated at a temperature of 28° C. in the presence of a series of 8 EM fields in the order stated: 360 MHz at 14 mV/cm for 5 hours; 365 MHz at 14 mV/cm for 5 hours; 370 MHz at 14 mV/cm for 5 hours; 380 MHz at 14 mV/cm for 5 hours; 360 MHz at 130 mV/cm for 30 hours; 365 MHz at 130 mV/cm for 30 hours; 370 MHz at 130 mV/cm for 30 hours; 375 MHz at 130 mV/cm for 30 hours. The increase in the amount of biologically available phosphorus was determined to be greater than 330 mg/ml of yeast culture.

5.3. Phosphorus-Balancing Yeast Cell Component

The phosphorus-balancing (P-balancing) yeasts of the invention also convert insoluble or biologically unavailable phosphorus-containing substances into soluble biologically available phosphorous compounds. However, the P-balancing yeast is preferably used when the level of phosphorus in the local environment is high. The conversion of insoluble or biologically unavailable phosphorus-containing substances into soluble biologically available phosphorous is sensitive to the level of phosphorus; at about 180 ppm or higher, the conversion is reduced while at about 60 ppm or lower, the conversion is increased.

In the present invention, the P-balancing yeast cells are preferably deployed in biologically fertilizer compositions that include an organic substrate that already contains a relatively significant level of soluble or biologically available phosphorous. For example, poultry manure contains a relatively high level of soluble phosphorus as compared to other kinds of manure.

According to the invention, yeast cells that are capable of P-balancing are prepared by culturing the cells in the presence of an electromagnetic field in an appropriate culture medium. The frequency of the electromagnetic field for activating or enhancing P-balancing function in yeasts can generally be found in the range of 300 MHz to 500 MHz. After the cells have been cultured for a sufficient period of time, the cells can be tested for their ability to decompose phosphorus-containing substances by methods well known in the art.

The method of the invention for making the P-balancing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1.5%. These carbon sources can be used individually, or several such carbon sources may be combined in the medium.

Among the inorganic salts which can be incorporated in the culture media are the customary salts capable of yielding sodium, potassium, calcium, sulfate, carbonate, and like ions. Non-limiting examples of nutrient inorganic salts are $CaCO_3$, $MgSO_4$, NaCl, and $CaSO_4$. Insoluble phosphorus-containing substances in a suitable form are also included in the media. Non-limiting examples include powder of dried sludge of >150 mesh. Other insoluble phosphorus-containing substances can also be used either separately or in combination.

TABLE 3

Composition for a culture medium for P-balancing yeast

| Medium Composition | Quantity |
|---|---|
| Sucrose | 15 g |
| NaCl | 1.2 g |
| MgSO$_4$•7H$_2$O | 0.2 g |
| CaCO$_3$•5H$_2$O | 3.0 g |
| CaSO$_4$•2H$_2$O | 0.3 g |
| KNO$_3$ | 0.3 g |
| Yeast extract paste | 0.5 g |
| Dried poultry manure | 1.2 g; Powder of >150 mesh |
| Autoclaved water | 1000 ml |

It should be noted that the composition of the media provided in Table 3 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of 10$^2$-10$^5$ cell/ml, preferably 3×10$^2$-10$^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 300 to about 500 MHz, or preferably in the range of 380.000 to 485.000 MHz. For example and without being limited by such examples, each EM field can have a frequency at about 380, 385, 390, 395, 400, 402, 405, 410, 415, 420, 422, 425, 430, 432, 435, 440, 445, 450, 455, 460, 465, 470, 480 or 485 MHz. The field strength of the EM field(s) is in the range of 90 to 300 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength.

Although any practical number of EM fields can be used within a series, it is preferred that the yeast culture be exposed to a total of 2, 3, 4, 5, 6, 7 or 8 different EM fields in a series.

Although the yeast cells will become activated even after a few hours of culturing in the presence of the EM field(s), and the yeast cells can be cultured in the presence of the EM field(s) for an extended period of time (e.g., two or more weeks), it is generally preferred that the activated yeast cells be allowed to multiply and grow in the presence of the EM field or EM fields for a total of about 230-480 hours.

For example, using an exemplary apparatus as depicted in FIG. 1, an initial field strength in the range of 50-150 mV/cm, usually at about 100 mV is used. After this first period of culture, the yeast cells are further incubated under substantially the same conditions for another period, except that the EM field strength is increased to a higher level in the range of 200-300 mV/cm, usually to about 250 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the P-balancing yeast cells may be recovered from the culture by various methods known in the art, and stored at a temperature below about 0° C. to 4° C. The P-balancing yeast cells may also be dried and stored in powder form.

The amount of biologically available phosphorus, such as $H_3PO_4$, $H_2PO_4^-$, and $HPO_4^{2-}$, in the culture can be determined by any methods known in the art, including but not limited to UV absorption spectroscopy. The increase can be calculated by the difference between the total amount of biologically available phosphorus in a culture with activated yeasts and the amount of phosphorus in the same medium with non-activated yeast. For example, 1 ml of *Saccharomyces cerevisiae* strain AS2.628 (2 to 5×10$^7$ yeasts/ml) is inoculated into 1000 ml of a medium containing 200 mg/l of $H_3PO_4$, $H_2PO_4^-$ and $HPO_4^{2-}$. The culture is incubated at a temperature of 28° C. in the presence of a series of 8 EM fields in the order stated: 385 MHz at 99 mV/cm for 12 hours; 415 MHz at 99 mV/cm for 12 hours; 440 MHz at 99 mV/cm for 12 hours; 460 MHz at 99 mV/cm for 12 hours; 385 MHz at 250 mV/cm for 48 hours; 415 MHz at 250 mV/cm for 48 hours; 440 MHz at 250 mV/cm for 24 hours; 460 MHz at 250 mV/cm for 24 hours. The increase in the amount of biologically available phosphorus was determined to be greater than 24%. The control did not show any significant change in the amount of biologically available phosphorus.

5.4. Potassium-Decomposing Yeast Cell Component

The potassium compound-decomposing (K-decomposing) yeasts of the invention converts insoluble potassium-containing substances, such as potassium mica, into soluble potassium so that they become available to plants.

In the present invention, the ability of a plurality of yeast cells to decompose insoluble potassium-containing substances is activated or enhanced, and the resulting K-decomposing yeast cells can be used as a component of the biological fertilizer compositions of the invention.

According to the present invention, yeast cells that are capable of K-decomposing are prepared by culturing the cells in the presence of an electromagnetic field in an appropriate culture medium. The frequency of the electromagnetic field for activating or enhancing K-decomposition in yeasts can generally be found in the range of 100 MHz-300 MHz. After the yeast cells have been cultured for a sufficient period of time, the cells can be tested for their ability to decompose potassium-containing substances by methods well known in the art.

The method of the invention for making the K-decomposing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 1.5%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $CaCO_3$, $MgSO_4$, $NaCl$, and $CaSO_4$. Insoluble potassium-containing substances in a suitable form are also included in the media. Non-limiting examples include powder of potassium mica of $\geq$200 mesh. Other insoluble potassium-containing substances can also be used either separately or combined.

TABLE 4

Composition for a culture medium for K-decomposing yeast

| Medium Composition | Quantity |
| --- | --- |
| Sucrose | 15 g |
| NaCl | 1.2 g |
| MgSO$_4$•7H$_2$O | 0.2 g |
| CaCO$_3$•5H$_2$O | 3.0 g |
| CaSO$_4$•2H$_2$O | 0.3 g |
| (NH$_4$)$_2$HPO$_4$ | 0.3 g |
| Yeast extract paste | 0.5 g |
| Potassium mica | 1.0 g, Powder of >200 mesh |
| Dried poultry manure | 1.2-3 g, Powder of >150 mesh |
| Autoclaved water | 1000 ml |

It should be noted that the composition of the media provided in Table 4 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of 10$^2$-10$^5$ cell/ml, preferably 3×10$^3$-10$^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 100 to about 300 MHz, preferably in the range of 190.000 to 285.000 MHz. For example and without being limited by such examples, each EM field can have a frequency at about 190, 195, 200, 205, 210, 215, 220, 225, 230, 235, 240, 245, 250, 255, 260, 265, 270, 275, 280, or 285 MHz. The field strength of the EM field(s) is in the range of 10 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 140-280 hours.

For example, using an exemplary apparatus as depicted in FIG. 1, an initial field strength in the range of 10-20 mV/cm, usually at about 125 mV/cm is used. After this first period of culture, the yeast cells are further incubated under substantially the same conditions for another period, except that the EM field strength is increased to a higher level in the range of 50-200 mV/cm, usually to about 125 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the K-decomposing yeast cells may be recovered from the culture by various methods known in the art, and stored at a temperature below about 0-4° C. The K-decomposing yeast cells may also be dried and stored in powder form.

Any methods known in the art can be used to test the cultured yeast cells for their ability to decompose insoluble potassium-containing substances. For example, 1 ml of *Saccharomyces cerevisiae* strain AS2.631 (2 to 5×10$^7$ cells/ml) was inoculated into 1000 ml of a medium according to Table 4. The culture was incubated at a temperature at 28° C. in the presence of a series of 8 EM fields in the order stated: 210 MHz at 14 mV/cm for 5 hours; 235 MHz at 14 mV/cm for 5 hours; 245 MHz at 14 mV/cm for 5 hours; 255 MHz at 14 mV/cm for 5 hours; 210 MHz at 120 mV/cm for 30 hours; 235 MHz at 120 mV/cm for 30 hours; 245 MHz at 120 mV/cm for 30 hours; 255 MHz at 120 mV/cm for 30 hours. A control was set up which contained non-activated cells of the same strain of yeasts. The amount of biologically available potassium K$^+$ in the culture can be determined by any methods known in the art, including but not limited to flame spectroscopy and/or atomic absorption spectrometry. The increase in potassium is calculated by the difference between the quantity of potassium in the medium of Table 4 after culturing and the basal level of potassium in the medium prior to culturing. The increase in the amount of biologically available potassium was determined to be greater than 120 mg/ml of cultured yeast cells. There was no significant change in the amount of potassium available in the control.

5.5. Complex Carbon-Decomposing Yeast Cell Component

The carbon-decomposing (C-decomposing) yeast of the invention converts complex, high molecular weight, carbon compounds and materials, in particular, complex carbohydrates, such as cellulose and lignin, into simple carbohydrates, such as pentoses and hexoses. Such simple carbohydrates are utilized by other yeast cells in the local environment to support their growth and activities.

In the present invention, the ability of yeast to decompose complex carbon compounds efficiently is activated or enhanced, and the resulting C-decomposing yeast cells can be used as a component of the biological fertilizer composition of the invention.

According to the present invention, yeast cells that are capable of C-decomposition are prepared by culturing the cells in the presence of an electromagnetic field in an appropriate culture medium. The frequency of the electromagnetic field for C-decomposition in yeasts can generally be found in the range of 1000 MHz-1200 MHz After the yeast cells have been cultured for a sufficient period of time, the cells can be tested for their ability to decompose complex carbon compounds by methods well known in the art.

The method of the invention for making the C-decomposing yeast cells is carried out in a liquid medium. The medium contains sources of nutrients assimilable by the yeast cells. Complex carbon-containing substances such as cellulose, lignin, coal powder, etc., in a suitable form can be used as sources of carbon in the culture medium. The exact quantity of the carbon source or sources utilized in the medium depends in part upon the other ingredients of the medium but, in general, the amount of simple carbohydrate usually varies between about 0.1% and 5% by weight of the medium and preferably between about 0.1% and 1%, and most preferably about 0.5%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $CaCO_3$, $MgSO_4$, $NaCl$, and $CaSO_4$.

TABLE 5

Composition for a culture medium for C-decomposing yeasts

| Medium Composition | Quantity |
| --- | --- |
| Cellulose | 3.0 g; Powder of >100 mesh |
| Dried poultry manure | 5 g; Powder of >150 mesh |
| NaCl | 0.6 g |
| $MgSO_4 \cdot 7H_2O$ | 0.3 g |
| $CaCO_3 \cdot 5H_2O$ | 1.5 g |
| $CaSO_4 \cdot 2H_2O$ | 0.4 g |
| $(NH_4)_2HPO_4$ | 0.3 g |
| Yeast extract paste | 0.5 g |
| $K_2HPO_4$ | 0.5 g |
| Autoclaved water | 1000 ml |

It should be noted that the composition of the media provided in Table 5 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-

$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 1000 to about 1200 MHz, preferably in the range of 1050.000 to 1160.000 MHz. For example and without being limited by such examples, each EM field can have a frequency at about 1050, 1055, 1060, 1065, 1070, 1075, 1080, 1085, 1090, 1095, 1100, 1105, 1110, 1115, 1120, 1125, 1130, 1135, 1140, 1145, 1150, 1155, or 1160 MHz. The field strength of the EM field(s) is in the range of 10 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 140-280 hours.

For example, using an exemplary apparatus as depicted in FIG. 1, an initial field strength in the range of 10-20 mV, usually at about 12.5 mV/cm is used. After this first period of culture, the yeast cells are further incubated under substantially the same conditions for another period, except that the EM field strength is increased to a higher level in the range of 100-200 mV/cm, usually to about 125 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m³, preferably 0.4 mol/m³. The oxygen level can be controlled by any conventional means known to one skilled in the art, including but not limited to stirring and/or bubbling.

At the end of the culturing process, the C-decomposing yeast cells may be recovered from the culture by various methods known in the art, and stored at a temperature below about 0-4° C. The C-decomposing yeast cells may also be dried and stored in powder form.

Any methods known in the art can be used to test the cultured yeast cells for their ability to decompose complex-carbon containing substances. For example, a change in the chemical oxygen demand (COD) of a sample can be used as an indication of the change in the concentration of complex-carbon containing substances in the sample. For example, 1 ml of the *Saccharomyces cerevisiae* strain AS2.982 (2 to $5 \times 10^7$ yeasts/ml) is inoculated into 30 ml of a medium according to Table 5. The culture is incubated at a temperature in the range of 20-28° C. for in the presence of a series of 8 EM fields in the order stated: 1050 MHz at 16 mV/cm for 5 hours; 1070 MHz at 16 mV/cm for 5 hours; 1090 MHz at 16 mV/cm for 5 hours; 1110 MHz at 16 mV/cm for 5 hours; 1050 MHz at 125 mV/cm for 30 hours; 1070 MHz at 125 mV/cm for 30 hours; 1090 MHz at 125 mV/cm for 30 hours; 1110 MHz at 125 mV/cm for 30 hours. After activation, based on a change in COD, the amount of carbohydrates in the culture was estimated to be greater than 330 mg/ml of yeast culture.

Alternatively, the amount of simple carbohydrates in the culture can then be determined by any methods known in the art, including but not limited to biochemical reactions, chromatography and molecular fluorescence spectroscopy.

5.6. Growth Factors Producing Yeast Cell Component

The growth factors producing (GF-producing) yeast of the present invention produces many vitamins and other nutrients, such as but not limited to, vitamin B-1, riboflavin (vitamin B-2), vitamin B-12, niacin (B-3), pyridoxine (B-6), pantothenic acid (B-5), folic acid, biotin, para-aminobenzoic acid, choline, inositol, in such amounts that can support the growth of other yeast strains.

The ability of yeast to overproduce growth factors is activated or enhanced by methods of this invention, and the resulting GF-producing yeast cells are included as a component of the biological fertilizer composition of the invention.

According to the present invention, yeast cells that are capable of overproducing growth factors are prepared by culturing the yeast cells in the presence of an electromagnetic field in an appropriate culture medium. The frequency of the electromagnetic field for activating or enhancing GF-production in yeasts can generally be found in the range of 1300 MHz-1500 MHz After the yeast cells have been cultured for a sufficient period of time, the cells can be tested for their ability to produce growth factors by methods well known in the art.

The method of the invention for making the GF-producing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $NH_4NO_3$, $K_2HPO_4$, $CaCO_3$, $MgSO_4$, NaCl, and $CaSO_4$.

TABLE 6

Composition for a culture medium for GF-producing yeasts

| Medium Composition | Quantity |
| --- | --- |
| Starch | 8.0 g; Powder of >120 mesh |
| NaCl | 0.3 g |
| $MgSO_4 \cdot 7H_2O$ | 0.2 g |
| $CaCO_3 \cdot 5H_2O$ | 0.5 g |
| $CaSO_4 \cdot 2H_2O$ | 0.2 g |

TABLE 6-continued

Composition for a culture medium for GF-producing yeasts

| Medium Composition | Quantity |
|---|---|
| $NH_4NO_3$ | 0.3 g |
| $K_2HPO_4$ | 0.8 g |
| Autoclaved water | 1000 ml |

It should be noted that the composition of the media provided in Table 6 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^3$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 1300 to about 1500 MHz, preferably in the range of 1340.000 to 1440.000 MHz. For example and without being limited by such examples, each EM field can have a frequency at about 1340, 1345, 1350, 1355, 1360, 1365, 1370, 1375, 1380, 1385, 1390, 1395, 1400, 1405, 1410, 1415, 1420, 1425, 1430, 1435, or 1440 MHz. The field strength of the EM field(s) is in the range of 20 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7 or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 140-280 hours.

For example, using an exemplary apparatus as depicted in FIG. 1, an initial field strength in the range of 20-40 mV/cm, usually at about 25 mV/cm is used. After this first period of culture, the yeast cells are further incubated under substantially the same conditions for another period, except that the amplitude is increased to a higher level in the range of 100-200 mV/cm, usually to about 125 mV. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m³, preferably 0.4 mol/m³. The oxygen level can be controlled by any conventional means known to one skilled in the art, including but not limited to stirring and/or bubbling.

At the end of the culturing process, the GF-producing yeast cells may be recovered from the culture by various methods known in the art, and stored at a temperature below about 0-4° C. The GF-producing yeast cells may also be dried and stored in powder form.

Any methods known in the art can be used to test the cultured yeast cells for their ability to overproduce growth factors, including but not limited to high performance liquid chromatography (HPLC). For example, 1 ml of activated or non-activated *Saccharomyces cerevisiae* strain AS2.413 (2 to $5 \times 10^7$ yeasts/ml) was inoculated into 1000 ml of a medium according to Table 6. The culture was incubated at a temperature of 28° C. in the presence of a series of 8 EM fields in the order stated: 1340 MHz at 28 mV/cm for 5 hours; 1350 MHz at 28 mV/cm for 5 hours; 1380 MHz at 28 mV/cm for 5 hours; 1390 MHz at 28 mV/cm for 5 hours; 1340 MHz at 135 mV/cm for 30 hours; 1350 MHz at 135 mV/cm for 30 hours; 1380 MHz at 135 mV/cm for 30 hours; 1390 MHz at 135 mV/cm for 30 hours. The amount of growth factors produced can be calculated by the difference between the total amount of vitamin B1, B2, B6, and B12 in a culture with activated or non-activated yeasts and the total amount of the same growth factors in the same medium without yeast. The increase in the amount of growth factors was determined to be greater than 350 mg/ml of activated yeast culture.

5.7. ATP-Producing Yeast Cell Component

The ATP-producing yeast of the present invention is capable of overproducing ATP in such amounts that can support the growth of other microbes in the biological fertilizer compositions.

In the present invention, the ability of yeast to overproduce ATP is activated or enhanced, and the resulting ATP-producing yeast cells can be used as a component of the biological fertilizer compositions of the invention.

According to the present invention, yeast cells that are capable of enhanced ATP-production are prepared by culturing the cells in the presence of an electric field in an appropriate culture medium. The frequency of the electromagnetic field for activating or enhancing ATP-production in yeasts can generally be found in the range of 1600 MHz-1800 MHz. After sufficient time is given for the cells to grow, the cells can be tested for their enhanced ability to produce ATP by methods well known in the art.

The method of the invention for making the ATP-producing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $K_2HPO_4$, $CaCO_3$, $MgSO_4$, $NaCl$, and $CaSO_4$.

TABLE 7

Composition for a culture medium for ATP-producing yeasts

| Medium Composition | Quantity |
| --- | --- |
| Starch | 10.0 g, >120 mesh |
| NaCl | 0.2 g |
| $MgSO_4 \cdot 7H_2O$ | 0.2 g |
| $CaCO_3 \cdot 5H_2O$ | 0.8 g |
| $CaSO_4 \cdot 2H_2O$ | 0.2 g |
| $NH_4NO_3$ | 0.2 g |
| $K_2HPO_4$ | 0.5 g |
| Autoclaved water | 1000 ml |

It should be noted that the composition of the media provided in Table 7 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 1600 to about 1800 MHz, preferably in the range of 1630.000 to 1730.000 MHz. For example and without being limited by such examples, each EM field can have a frequency at about 1630, 1635, 1640, 1645, 1650, 1655, 1660, 1665, 1670, 1675, 1680, 1685, 1690, 1695, 1700, 1705, 1710, 1715, 1720, 1725, or 1730 MHz. The field strength of the EM field(s) is in the range of 20 to 200 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 160-300 hours.

For example, using an exemplary apparatus as depicted in FIG. 1, an initial field strength in the range of 20-40 mV/cm, usually at about 30 mV/cm is used. After this first period of culture, the yeast cells are further incubated under substantially the same conditions for another period, except that the amplitude is increased to a higher level in the range of 100-200 mV/cm, usually to about 150 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m³, preferably 0.4 mol/m³. The oxygen level can be controlled by any conventional means known to one skilled in the art, including but not limited to stirring and/or bubbling.

At the end of the culturing process, the ATP-producing yeast cells may be recovered from the culture by various methods known in the art, and stored at a temperature below about 0-4° C. The ATP-producing yeast cells may also be dried and stored in powder form.

Any methods known in the art can be used to test the cultured yeast cells for their ability to overproduce ATP, including but not limited to HPLC. For example, 1 ml of the activated yeast culture (2 to $5 \times 10^7$ yeasts/ml) was inoculated into 1000 ml of a medium according to Table 7. The culture was incubated at a temperature of 28° C. in the presence of a series of 8 EM fields in the order stated: 1635 MHz at 29 mV/cm for 10 hours; 1655 MHz at 29 mV/cm for 10 hours; 1675 MHz at 29 mV/cm for 10 hours; 1695 MHz at 29 mV/cm for 10 hours; 1635 MHz at 150 mV/cm for 30 hours; 1655 MHz at 150 mV/cm for 30 hours; 1675 MHz at 150 mV/cm for 30 hours; 1695 MHz at 150 mV/cm for 30 hours. The amount of ATP produced can be calculated by the difference between the total amount of ATP in a culture with yeasts and the amount of ATP in the same medium without yeast. Using activated *Saccharomyces cerevisiae* strain AS2.536, the amount of ATP in the culture was determined to be 170 mg/ml of yeast culture.

5.8. Pathogen-Suppressing Yeast Cell Component

The present invention also provides yeast cells that are capable of suppressing the proliferation of pathogenic microorganisms that are present in the materials used in the organic substrate component of the biological fertilizer. Typically, due to an abundance of nutrients present in the organic substrate material for such pathogenic microorganisms, the numbers of pathogens increase rapidly over a period of time. However, in the presence of the pathogen-suppressing yeasts of the invention, the numbers of pathogens in the organic substrate material remains unchanged, or decreases over time. Without being bound by any theory or mechanism, the inventor believes that the presence of the pathogen-suppressing yeasts in the organic substrate material creates an environment that is unfavorable for the growth of pathogenic microorganisms.

According to the invention, the ability of yeasts to affect/control the numbers of pathogens is activated or enhanced by culturing the yeasts in the presence of an electromagnetic field. The resulting pathogen-suppressing yeast cells are used as a component in the biological fertilizer compositions of the invention.

The frequency of the electromagnetic field for activating or enhancing the ability of yeasts to control the numbers of pathogenic microorganisms can generally be found in the range of 30 MHz to 50 MHz. After sufficient time is given for the yeast cells to grow, the cells can be tested for their ability to affect/control the number of pathogens by methods well known in the art.

The method of the invention for making pathogen-suppressing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $K_2HPO_4$, $CaCO_3$, $MgSO_4$, NaCl, and $CaSO_4$.

TABLE 8

Composition for a culture medium for Pathogen-Suppressing yeasts

| Medium Composition | Quantity |
|---|---|
| Soluble Starch | 8.0 g |
| Sucrose | 5 g |
| NaCl | 0.2 g |
| $MgSO_4 \cdot 7H_2O$ | 0.2 g |
| $CaCO_3 \cdot 5H_2O$ | 0.5 g |
| $CaSO_4 \cdot 2H_2O$ | 0.2 g |
| Peptone | 1.5 g |
| $K_2HPO_4$ | 0.5 g |
| Autoclaved water | 400 ml |
| Poultry manure extract | 600 ml |

The poultry manure extract for the culture medium is prepared by incubating 500 g of poultry manure in about 600 ml of warm water (at 35° C. to 40° C.) for 24 hours at 30-37° C., and filtering the fluid to remove particulate matters. It should be noted that the composition of the media provided in Table 8 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of about 30.000 to about 50.000 MHz. For example and without being limited by such examples, each EM field can have a frequency at about 30, 31, 32, 33, 34, 35, 36, 37, 38, 39, 40, 41, 42, 43, 44, 45, 46, 47, 48, 49, or 50 MHz. The field strength of the EM field(s) is in the range of 0.5 to 200 mV/cm, preferably 10 to 180 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 144-272 hours.

For example, using an exemplary apparatus as depicted in FIG. 1, an initial field strength in the range of 10-30 mV/cm, usually at about 25 mV/cm is used. After this first period of culture, the yeast cells are further incubated under substantially the same conditions for another period, except that the amplitude is increased to a higher level in the range of 100-200 mV/cm, usually to about 150 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the pathogen-suppressing yeast cells may be recovered from the culture by various methods known in the art, and stored at about 0° C. to 4° C. The pathogen-suppressing yeast cells may also be dried and stored in powder form.

The ability of the pathogen-suppressing yeasts to control the numbers of pathogens can be determined by any methods known in the art for enumerating microorganisms, such as optical density, plating out dilutions on solid media for counting, or counting individual cells under a microscope. Stains may be applied to distinguish or identify different strains or species of microorganisms present in a sample, or to determine their viability. When a range of pathogenic microorganisms are expected to be affected by the pathogen-suppressing yeasts, the numbers of more than one representative species of pathogenic microorganisms can be monitored to assess the performance of the pathogen-suppressing yeasts.

For example, samples of organic substrate material containing a known concentration of pathogenic microorganisms are cultured under the same conditions for a same period of time in the presence of different concentrations of pathogen-suppressing yeasts, and as negative control, the same strain of yeasts that have not been treated according to the culturing methods of the invention. A sample without any added yeast may also be included to determine the growth of pathogens under normal circumstances. The numbers of pathogens before and after the culture period are determined and compared.

A one liter culture containing at least $10^{10}$ cells of a pathogenic microorganism per ml is prepared. One ml of activated yeast cells (containing 2 to $5 \times 10^7$ yeasts per ml) is added to the one liter culture of pathogenic microorganism and incubated at 30° C. for 24 hours. Controls are included which contained non-activated yeast cells or no yeasts. The numbers of microorganisms in the respective cultures are then determined and compared. The following are several examples in which a particular species of pathogenic bacteria was studied.

Using cells of *Saccharomyces cerevisiae* strain IFFI1037 which had been cultured in the presence of a series of 8 EM fields in the order stated: 30 MHz at 26 mV/cm for 12 hours; 36 MHz at 26 mV/cm for 12 hours; 43 MHz at 26 mV/cm for 12 hours; 47 MHz at 26 mV/cm for 12 hours; 30 MHz at 150 mV/cm for 24 hours; 36 MHz at 150 mV/cm for 24 hours; 43 MHz at 150 mV/cm for 24 hours; 47 MHz at 150 mV/cm for 24 hours. The number of *Staphylococcus aureus* in a sample was reduced by more than 2.7% relative to the control with no yeasts. There was no significant change in the number of pathogens in the control containing non-activated cells.

Using cells of *Saccharomyces cerevisiae* strain IFFI1021 which had been cultured in the presence of a series of 8 EM fields in the order stated: 30 MHz at 26 mV/cm for 12 hours; 36 MHz at 26 mV/cm for 12 hours; 42 MHz at 26 mV/cm for 12 hours; 49 MHz at 26 mV/cm for 12 hours; 30 MHz at 150 mV/cm for 24 hours; 36 MHz at 150 mV/cm for 24 hours; 42 MHz at 150 mV/cm for 24 hours; 49 MHz at 150 mV/cm for 24 hours. The number of *Diplococcus pneumoniae* in a sample was reduced by more than 2.8% relative to the control with no yeasts. There was no significant change in the number of pathogens in the control containing non-activated cells.

Using cells of *Saccharomyces cerevisiae* strain IFFI1051 which had been cultured in the presence of a series of 8 EM fields in the order stated: 35 MHz at 26 mV/cm for 12 hours; 39 MHz at 26 mV/cm for 12 hours; 43 MHz at 26 mV/cm for 12 hours; 47 MHz at 26 mV/cm for 12 hours; 35 MHz at 150 mV/cm for 24 hours; 39 MHz at 150 mV/cm for 24 hours; 43 MHz at 150 mV/cm for 24 hours; 47 MHz at 150 mV/cm for 24 hours. The number of *Bacillus anthracis* in a sample was reduced by more than 3.1% relative to the control with no yeasts. There was no significant change in the number of pathogens in the control containing non-activated cells.

Using cells of *Saccharomyces cerevisiae* strain IFFI1331 which had been cultured in the presence of a series of 8 EM fields in the order stated: 33 MHz at 26 mV/cm for 12 hours; 36 MHz at 26 mV/cm for 12 hours; 45 MHz at 26 mV/cm for 12 hours; 47 MHz at 26 mV/cm for 12 hours; 33 MHz at 150 mV/cm for 24 hours; 36 MHz at 150 mV/cm for 24 hours; 45 MHz at 150 mV/cm for 24 hours; 47 MHz at 150 mV/cm for 24 hours. The number of *Mycobacterium tuberculosis* in a sample was reduced by more than 2.9% relative to the control with no yeasts. There was no significant change in the number of pathogens in the control containing non-activated cells.

Using cells of *Saccharomyces cerevisiae* strain IFFI1345 which had been cultured in the presence of a series of 8 EM fields in the order stated: 30 MHz at 26 mV/cm for 12 hours; 34 MHz at 26 mV/cm for 12 hours; 38 MHz at 26 mV/cm for 12 hours; 49 MHz at 26 mV/cm for 12 hours; 30 MHz at 150 mV/cm for 24 hours; 34 MHz at 150 mV/cm for 24 hours; 38 MHz at 150 mV/cm for 24 hours; 49 MHz at 150 mV/cm for 24 hours. The number of *Escherichia coli* in a sample was reduced by more than 48% relative to the control with no yeasts. There was no significant change in the number of pathogens in the control containing non-activated cells.

Using cells of *Saccharomyces cerevisiae* strain IFFI1211 which had been cultured in the presence of a series of 8 EM fields in the order stated: 30 MHz at 26 mV/cm for 12 hours; 33 MHz at 26 mV/cm for 12 hours; 36 MHz at 26 mV/cm for 12 hours; 38 MHz at 26 mV/cm for 12 hours; 30 MHz at 150 mV/cm for 24 hours; 33 MHz at 150 mV/cm for 24 hours; 36 MHz at 150 mV/cm for 24 hours; 38 MHz at 150 mV/cm for 24 hours. The number of *Salmonella* species bacteria in a sample was reduced by more than 66% relative to the control with no yeasts. There was no significant change in the number of pathogens in the control containing non-activated cells.

5.9. Yeast Cell Component that Decomposes Undesirable Chemicals

The present invention further provides yeast cells that are capable of degrading undesirable chemicals, such as antibiotics, that are typically found in manure.

According to the invention, the ability of yeasts to degrade antibiotics is activated or enhanced by culturing the yeasts in the presence of an electromagnetic field. The resulting yeast cells can be used as a component in the biological fertilizer compositions of the invention.

The frequency of the electromagnetic field for activating or enhancing the ability of yeasts to degrade undesirable chemicals, in particular antibiotics, can generally be found in the range of about 70 MHz to about 100 MHz. After sufficient time is given for the yeast cells to grow, the yeast cells can be tested for their enhanced ability to decompose antibiotics by methods well known in the art. Antibiotics degraded by the yeasts of the invention include but are not limited to molecules within the families of beta-lactams, tetracyclines, polypeptides, glycopeptides, aminoglycosides, and macrolides.

The method of the invention for making antibiotics-degrading yeasts is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $K_2HPO_4$, $CaCO_3$, $MgSO_4$, NaCl, and $CaSO_4$.

TABLE 9

Composition for a culture medium for yeasts that degrade undesirable chemicals

| Medium Composition | Quantity |
|---|---|
| Soluble Starch | 8.0 g; >120 mesh |
| Sucrose | 5 g |
| NaCl | 0.2 g |
| $MgSO_4•7H_2O$ | 0.2 g |
| $CaCO_3•5H_2O$ | 0.5 g |
| $CaSO_4•2H_2O$ | 0.2 g |
| Peptone | 1.5 g |
| $K_2HPO_4$ | 0.5 g |
| Autoclaved water | 1000 ml |
| poultry manure extract | 600 ml |

The poultry manure extract for the culture medium is prepared by incubating 500 g of fresh poultry manure in about 600 ml of warm water (at 35-40° C.) for 24 hours at 30-37° C., and filtering the fluid to remove particulate matters. It should be noted that the composition of the media provided in Table 9 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3\times10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of 70.000 to 100.000 MHz. For example and without being limited by such examples, each EM field can have a frequency at about 70, 71, 72, 73, 74, 75, 76, 77, 78, 79, 80, 81, 82, 83, 84, 85, 86, 87, 88, 89, 90, 91, 92, 93, 94, 95, 96, 97, 98, or 100 MHz. The field strength of the EM field(s) is in the range of 40 to 250 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., one or more weeks), it is generally preferred that the activated yeast cells be allowed to multiply and grow in the presence of the EM field or EM fields for a total of about 180-328 hours.

For example, using an exemplary apparatus as depicted in FIG. 1, an initial field strength in the range of 40-60 mV/cm, usually at about 50 mV is used. After this first period of culture, the yeast cells are further incubated under substantially the same conditions for another period, except that the amplitude is increased to a higher level in the range of 100-250 mV/cm, usually to about 200 mV/cm. The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the yeast cells may be recovered from the culture by various methods known in the art, and stored at a temperature below about 0° C. to 4° C. The recovered yeast cells may also be dried and stored in powder.

To determine the activity of the activated yeast cells towards an antibiotic compound, methods well known in the art, such as HPLC, can be used to measure the amounts of the antibiotic compound in a test sample at various time point and under different incubation conditions. For example, a known amount of an antibiotic (up to 100 mg per liter) is added to 10 liter of an aqueous extract of the manure. Then, 0.1 ml each of activated and non-activated yeasts (at least 10$^7$ cells/ml) are added to the 10 liter samples containing the antibiotics, and incubated for 24 hours at 28° C. A control is also included which does not contain any yeast cells. After 24 hours, the amounts of antibiotics remaining in the extracts are determined and compared by performing HPLC-on samples of the extracts.

Using cells of *Saccharomyces cerevisiae* strain AS2.293 which had been cultured in the presence of a series of 8 EM fields in the order stated: 77 MHz at 48 mV/cm for 15 hours; 83 MHz at 48 mV/cm for 15 hours; 90 MHz at 48 mV/cm for 15 hours; 96 MHz at 48 mV/cm for 15 hours; 77 MHz at 200 mV/cm for 30 hours; 83 MHz at 200 mV/cm for 30 hours; 90 MHz at 200 mV/cm for 30 hours; 96 MHz at 200 mV/cm for 30 hours. The amount of penicillin G in a sample was reduced by more than 23% relative to the control with no yeasts. There was no significant change in the concentration of the antibiotic in the control containing non-activated cells.

Using cells of *Saccharomyces cerevisiae* strain IFFI1063 which had been cultured in the presence of a series of 8 EM fields in the order stated: 70 MHz at 48 mV/cm for 15 hours; 73 MHz at 48 mV/cm for 15 hours; 88 MHz at 48 mV/cm for 15 hours; 98 MHz at 48 mV/cm for 15 hours; 70 MHz at 200 mV/cm for 30 hours; 73 MHz at 200 mV/cm for 30 hours; 88 MHz at 200 mV/cm for 30 hours; 98 MHz at 200 mV/cm for 30 hours. The amount of chlorotetracycline in a sample was reduced by more than 31% relative to the control with no yeasts. There was no significant change in the concentration of the antibiotic in the control containing non-activated cells.

Using cells of *Saccharomyces cerevisiae* strain IFFI1221 which had been cultured in the presence of a series of 8 EM fields in the order stated: 70 MHz at 48 mV/cm for 15 hours; 74 MHz at 48 mV/cm for 15 hours; 88 MHz at 48 mV/cm for 15 hours; 98 MHz at 48 mV/cm for 15 hours; 70 MHz at 200 mV/cm for 30 hours; 74 MHz at 200 mV/cm for 30 hours; 88 MHz at 200 mV/cm for 30 hours; 98 MHz at 200 mV/cm for 30 hours. The amount of oxytetracycline in a sample was reduced by more than 28% relative to the control with no yeasts. There was no significant change in the concentration of the antibiotic in the control containing non-activated cells.

Using cells of *Saccharomyces cerevisiae* strain IFFI1340 which had been cultured in the presence of a series of 8 EM fields in the order stated: 71 MHz at 48 mV/cm for 15 hours; 73 MHz at 48 mV/cm for 15 hours; 77 MHz at 48 mV/cm for 15 hours; 88 MHz at 48 mV/cm for 15 hours; 71 MHz at 200 mV/cm for 30 hours; 73 MHz at 200 mV/cm for 30 hours; 77 MHz at 200 mV/cm for 30 hours; 88 MHz at 200 mV/cm for 30 hours. The amount of doxycycline in a sample was reduced by more than 33% relative to the control with no yeasts. There was no significant change in the concentration of the antibiotic in the control containing non-activated cells.

Using cells of *Saccharomyces cerevisiae* strain IFFI1215 which had been cultured in the presence of a series of 8 EM fields in the order stated: 70 MHz at 48 mV/cm for 15 hours; 75 MHz at 48 mV/cm for 15 hours; 82 MHz at 48 mV/cm for 15 hours; 85 MHz at 48 mV/cm for 15 hours; 70 MHz at 200 mV/cm for 30 hours; 75 MHz at 200 mV/cm for 30 hours; 82 MHz at 200 mV/cm for 30 hours; 85 MHz at 200 mV/cm for 30 hours. The amount of tetracycline in a sample was reduced by more than 26% relative to the control with no yeasts. There was no significant change in the concentration of the antibiotic in the control containing non-activated cells.

Using cells of *Saccharomyces cerevisiae* strain IFFI1213 which had been cultured in the presence of a series of 8 EM fields in the order stated: 70 MHz at 48 mV/cm for 15 hours; 73 MHz at 48 mV/cm for 15 hours; 80 MHz at 48 mV/cm for 15 hours; 96 MHz at 48 mV/cm for 15 hours; 70 MHz at 200 mV/cm for 30 hours; 73 MHz at 200 mV/cm for 30 hours; 80 MHz at 200 mV/cm for 30 hours; 96 MHz at 200 mV/cm for 30 hours. The amount of streptomycin in a sample was reduced by more than 31% relative to the control with no yeasts. There was no significant change in the concentration of the antibiotic in the control containing non-activated cells.

Using cells of *Saccharomyces cerevisiae* strain IFFI1206 which had been cultured in the presence of a series of 8 EM fields in the order stated: 71 MHz at 48 mV/cm for 15 hours; 78 MHz at 48 mV/cm for 15 hours; 86 MHz at 48 mV/cm for 15 hours; 98 MHz at 48 mV/cm for 15 hours; 71 MHz at 200 mV/cm for 30 hours; 78 MHz at 200 mV/cm for 30 hours; 86 MHz at 200 mV/cm for 30 hours; 98 MHz at 200 mV/cm for 30 hours. The amount of kanamycin in a sample was reduced by more than 25% relative to the control with no yeasts. There was no significant change in the concentration of the antibiotic in the control containing non-activated cells.

Using cells of *Saccharomyces cerevisiae* strain IFFI1211 which had been cultured in the presence of a series of 8 EM fields in the order stated: 73 MHz at 48 mV/cm for 15 hours; 79 MHz at 48 mV/cm for 15 hours; 88 MHz at 48 mV/cm for 15 hours; 98 MHz at 48 mV/cm for 15 hours; 73 MHz at 200 mV/cm for 30 hours; 79 MHz at 200 mV/cm for 30 hours; 88 MHz at 200 mV/cm for 30 hours; 98 MHz at 200 mV/cm for 30 hours. The amount of erythromycin in a sample was reduced by more than 27% relative to the control with no yeasts. There was no significant change in the concentration of the antibiotic in the control containing non-activated cells.

Using cells of *Saccharomyces cerevisiae* strain IFFI1210 which had been cultured in the presence of a series of 8 EM fields in the order stated: 70 MHz at 48 mV/cm for 15 hours; 77 MHz at 48 mV/cm for 15 hours; 84 MHz at 48 mV/cm for 15 hours; 93 MHz at 48 mV/cm for 15 hours; 70 MHz at 200 mV/cm for 30 hours; 77 MHz at 200 mV/cm for 30 hours; 84 MHz at 200 mV/cm for 30 hours; 93 MHz at 200 mV/cm for 30 hours. The amount of spiramycin in a sample was reduced by more than 22% relative to the control with no yeasts. There was no significant change in the concentration of the antibiotic in the control containing non-activated cells.

Using cells of *Saccharomyces cerevisiae* strain IFFI1260 which had been cultured in the presence of a series of 8 EM fields in the order stated: 75 MHz at 48 mV/cm for 15 hours; 78 MHz at 48 mV/cm for 15 hours; 81 MHz at 48 mV/cm for 15 hours; 95 MHz at 48 mV/cm for 15 hours; 75 MHz at 200 mV/cm for 30 hours; 78 MHz at 200 mV/cm for 30 hours; 81 MHz at 200 mV/cm for 30 hours; 95 MHz at 200 mV/cm for 30 hours. The amount of bacitracin in a sample was reduced by more than 17% relative to the control with no yeasts. There was no significant change in the concentration of the antibiotic in the control containing non-activated cells.

5.10. Odor-Reducing Yeast Cell Component

The present invention also provides yeast cells that are capable of reducing the odor of poultry manure. Without being bound by any theory, the inventor believes that the yeast cells of the invention are capable of reducing the odor of poultry manure by modifying or decomposing known and unknown compounds in the manure that are malodorous. However, it is not necessary to demonstrate that such compounds have been decomposed. It is sufficient so long as the odor is reduced as determined subjectively by a panel of subjects, after the yeast cells of the invention have been used.

According to the present invention, yeast cells that are capable of reducing the odor of organic materials are prepared by culturing the cells in the presence of an electromagnetic field in an appropriate culture medium. The frequency of the electromagnetic field for activating or enhancing this ability in yeasts can generally be found in the range of about 2160 to about 2380 MHz. After sufficient time is given for the yeast cells to grow, the yeast cells can be tested for their ability to reduce the odor of organic materials by methods well known in the art.

The method of the invention for making the odor-reducing yeast cells is carried out in a liquid medium. The medium contains sources of nutrients assimilable by the yeast cells. In general, carbohydrates such as sugars, for example, sucrose, glucose, fructose, dextrose, maltose, xylose, and the like and starches, can be used either alone or in combination as sources of assimilable carbon in the culture medium. The exact quantity of the carbohydrate source or sources utilized in the medium depends in part upon the other ingredients of the medium but, in general, the amount of carbohydrate usually varies between about 0.1% and 5% by weight of the medium and preferably between about 0.5% and 2%, and most preferably about 0.8%. These carbon sources can be used individually, or several such carbon sources may be combined in the medium.

Among the inorganic salts which can be incorporated in the culture media are the customary salts capable of yielding sodium, calcium, phosphate, sulfate, carbonate, and like ions. Non-limiting examples of nutrient inorganic salts are $(NH_4)_2HPO_4$, $K_2HPO_4$, $CaCO_3$, $MgSO_4$, $NaCl$, and $CaSO_4$.

TABLE 10

Composition for a culture medium for yeasts that reduce odor

| Medium Composition | Quantity |
| --- | --- |
| Poultry manure | 100 g |
| NaCl | 0.2 g |
| $MgSO_4 \cdot 7H_2O$ | 0.2 g |
| $CaCO_3 \cdot 5H_2O$ | 0.5 g |
| $CaSO_4 \cdot 2H_2O$ | 0.2 g |
| $K_2HPO_4$ | 0.5 g |
| Autoclaved water | 900 ml |

It should be noted that the composition of the media provided in Table 10 is not intended to be limiting. Various modifications of the culture medium may be made by those skilled in the art, in view of practical and economic considerations, such as the scale of culture and local supply of media components.

The process can be initiated by inoculating 100 ml of medium with 1 ml of an inoculum of the selected yeast strain(s) at a cell density of $10^2$-$10^5$ cell/ml, preferably $3 \times 10^2$-$10^4$ cell/ml. The process can be scaled up or down according to needs. The yeast culture is grown in the presence of an electromagnetic (EM) field, or a series of EM fields. If a series of EM fields are applied, the yeast culture can remain in the same container and use the same set of electromagnetic wave generator and emitters when switching from one EM field to another EM field.

The EM field(s), which can be applied by any means known in the art, can each have a frequency in the range of 2160.000 to 2380.000 MHz, and preferably in the ranges of 2160 to 2250 MHz or 2280 to 2380 MHz. For example and without being limited by such examples, each EM field can have a frequency at about 2160, 2165, 2170, 2175, 2180, 2185, 2190, 2195, 2200, 2205, 2210, 2215, 2220, 2225, 2230, 2235, 2240, 2245, 2250, 2280, 2285, 2290, 2295, 2300, 2305, 2315, 2320, 2325, 2330, 2335, 2340, 2345, 2350, 2355, 2360, 2365, 2370, 2375, or 2380 MHz. The field strength of the EM field(s) is in the range of 0.5 to 320 mV/cm, preferably 30 to 300 mV/cm. If a series of EM fields are applied, the EM fields can each have a different frequency within the stated range, or a different field strength within the stated range, or different frequency and field strength within the stated ranges. In a preferred embodiment, the EM field(s) at the beginning of a series have a lower EM field strength than later EM field(s), such that the yeast cell culture are exposed to EM fields of progressively increasing field strength. Although any practical number of EM fields can be used within a series, it is preferred that the yeast culture be exposed to a total of 2, 3, 4, 5, 6, 7, or 8 different EM fields in a series.

Although the yeast cells will become activated even after a few hours of culturing in the presence of the EM field(s), and the yeast cells can be cultured in the presence of the EM field(s) for an extended period of time (e.g., two or more weeks), it is generally preferred that the activated yeast cells be allowed to multiply and grow in the presence of the EM field or EM fields for a total of about 80-320 hours.

The process of the invention is carried out at temperatures ranging from about 23° to 30° C.; however, it is preferable to conduct the process at 25° to 28° C. The culturing process may preferably be conducted under conditions in which the concentration of dissolved oxygen is between 0.025 to 0.8 mol/m$^3$, preferably 0.4 mol/m$^3$. The oxygen level can be controlled by any conventional means known to one skilled in the art, including but not limited to stirring and/or bubbling.

At the end of the culturing process, the yeast cells may be recovered from the culture by various methods known in the art, and stored at a temperature below about 0-4° C. The recovered yeast cells may also be dried and stored in powder form.

Any methods known in the art can be used to test the cultured yeast cells for their ability to reduce the odor of organic materials. The amount of malodorous chemicals such as hydrogen sulfide, ammonia, indole, p-cresol, skatol, and organic acids present in a test sample of organic material can be determined by any methods known in the art, including but not limited to gas phase chromatography, olfactometry, mass spectrometry, or the use of an odor panel.

To determine the activity of the activated yeast cells towards an malodorous compound, methods well known in the art, such as HPLC or mass spectrometry (e.g., VG micromass), can be used to measure the amounts of the malodorous compound in a test sample at various time point and under different incubation conditions. For example, a known amount of a malodorous compound (up to 100 mg per liter) is added to 10 liter of an aqueous extract of manure. Then, 0.1 ml of activated and non-activated yeasts (at least 10$^7$ cells/ml) are added to the 10 liter samples containing the antibiotics, and incubated for 24 hours at 28° C. A control is also included which does not contain any yeast cells. After 24 hours, the amounts of the malodorous compounds remaining in the extracts are determined and compared.

Accordingly, the odor caused by hydrogen sulfide and other related sulfur-containing or sulfhydryl (SH-) containing molecules can be reduced by yeasts cultured in the presence of an EM field that is in the range of 2160.000 to 2250.000. Using cells of *Saccharomyces cerevisiae* strain AS2.559 which had been cultured in the presence of a series of four EM fields in the order stated: 2165 MHz at 240 mV/cm for 20 hours; 2175 MHz at 240 mV/cm for 20 hours; 2200 MHz at 240 mV/cm for 20 hours; and 2235 MHz at 240 mV/cm for 20 hours, the amount of hydrogen sulfide in a sample was reduced by more than 13% relative to the control containing no yeasts. There was no significant reduction in the malodorous compound in the sample containing non-activated yeasts.

The odor caused by ammonia and related NH-containing compounds can be reduced by yeasts cultured in the presence of an EM field that is in the range of 2160.000 to 2250.000. Using cells of *Saccharomyces cerevisiae* strain AS2.423 which had been cultured in the presence of a series of four EM fields in the order stated: 2160 MHz at 250 mV/cm for 20 hours; 2175 MHz at 250 mV/cm for 20 hours; 2210 MHz at 250 mV/cm for 20 hours; and 2245 MHz at 250 mV/cm for 10 hours, the amount of ammonia in a sample was reduced by more than 11% relative to the control containing no yeasts. There was no significant reduction in the malodorous compound in the sample containing non-activated yeasts.

The odor caused by indole and other related molecules, such as skatol, can be reduced by yeasts cultured in the presence of an EM field that is in the range of 2160.000 to 2250.000. Using cells of *Saccharomyces cerevisiae* strain AS2.612 which had been cultured in the presence of a series of four EM fields in the order stated: 2165 MHz at 240 mV/cm for 40 hours; 2180 MHz at 240 mV/cm for 20 hours; 2200 MHz at 240 mV/cm for 40 hours; and 2220 MHz at 240 mV/cm for 20 hours, the amount of indole in a sample was reduced by more than 15% relative to the control containing no yeasts. There was no significant reduction in the malodorous compound in the sample containing non-activated yeasts.

The odor caused by organic acids (such as formic acid, acetic acid, propanoic acid, butyric acid, and other volatile fatty acids) can be reduced by yeasts cultured in the presence of an EM field that is in the range of 2280.000 to 2380.000. Using cells of *Saccharomyces cerevisiae* strain AS2.53 which had been cultured in the presence of a series of four EM fields in the order stated: 2315 MHz at 290 mV/cm for 30 hours; 2335 MHz at 290 mV/cm for 10 hours; 2355 MHz at 290 mV/cm for 20 hours; and 2375 MHz at 290 mV/cm for 10 hours, the amount of acetic acid in a sample was reduced by more than 19% relative to the control containing no yeasts. There was no significant reduction in the malodorous compound in the sample containing non-activated yeasts.

The odor caused by methylamine, dimethylamine, trimethylamine, and other aliphatic substituted amines can be reduced by yeasts cultured in the presence of an EM field that is in the range of 2160.000 to 2250.000. Using cells of *Saccharomyces cerevisiae* strain AS2.541 which had been cultured in the presence of a series of four EM fields in the order stated: 2160 MHz at 250 mV/cm for 20 hours; 2190 MHz at 250 mV/cm for 10 hours; 2210 MHz at 250 mV/cm for 40 hours; and 2250 MHz at 250 mV/cm for 40 hours, the amount of methyl-substituted amines in a sample was reduced by more than 23% relative to the control containing no yeasts. There was no significant reduction in the malodorous compound in the sample containing non-activated yeasts.

The odor caused by p-cresol and related compounds can be reduced by yeasts cultured in the presence of an EM field that is in the range of 2280.000 to 2380.000. Using cells of *Saccharomyces cerevisiae* strain AS2.163 which had been cultured in the presence of a series of four EM fields in the order stated: 2300 MHz at 98 mV/cm for 20 hours; 2370 MHz at 98 mV/cm for 15 hours; 2300 MHz at 250 mV/cm for 20 hours; and 2370 MHz at 250 mV/cm for 30 hours, the amount of p-cresol in a sample was reduced by more than 23% relative to the control containing no yeasts. There was no significant reduction in the malodorous compound in the sample containing non-activated yeasts.

5.11. Formation of Symbiosis-Like Relationships

In another embodiment of the present invention, yeast cells with the newly activated or enhanced ability to (1) fix nitrogen, (2) decompose phosphorus-containing minerals or compounds, (3) balance phosphorus compounds, (4) decompose is insoluble potassium-containing minerals or compounds, and (5) decompose complex carbon compounds as described in Sections 5.1-5.5 are combined and cultured so that they form a symbiosis-like relationship whereby they can grow together without substantially relying on outside supplies of biological available nitrogen, phosphorus, potassium, and carbon nutrients. The nutrients needed for growth are supplied by the respective nutrient-producing yeast strain within the fertilizer composition by converting biologically-unavailable nutrients from various sources into available nutrients. The activity of each of the yeast strains in producing the respective types of nutrient relates in part to the needs of other yeast cells as well as the plants. As a result, soluble, biologically-available nutrients will be converted when needed, thereby avoiding excess losses due to, for example, leaching.

The optional process which can be used to improve the performance of the biological fertilizer is described as follows. At least four strains of yeasts prepared according to Sections 5.1-5.5 are mixed and cultured in the presence of an electromagnetic field in an appropriate liquid medium. The medium contains nitrogen, phosphorus, potassium, and carbon nutrients in biologically unavailable forms. As non-limiting examples, atmospheric nitrogen is used as the source of nitrogen nutrient, powder of phosphate rock is used as the source of phosphorus nutrient, powder of potassium mica is used as the source of potassium nutrient, and powdered cellulose is used as the source of complex carbon nutrient. Other forms of insoluble phosphorus- and potassium-containing substances and complex carbon compounds may also be used in place of or in combination with any of the above-identified minerals as sources of phosphorus, potassium, and carbon nutrients. Among the inorganic salts which can be incorporated in the culture media are the customary salts capable of yielding sodium, calcium, sulfate, carbonate, and like ions. Non-limiting examples of nutrient inorganic salts are $CaCO_3$, $MgSO_4$, NaCl, and $CaSO_4$.

TABLE 11

Composition for a culture medium for formation of symbiosis-like relation

| Medium Composition | Quantity |
|---|---|
| NaCl | 0.5 g |
| $MgSO_4 \cdot 7H_2O$ | 0.4 g |
| $CaCO_3 \cdot 5H_2O$ | 3.0 g |
| $CaSO_4 \cdot 2H_2O$ | 0.3 g |
| Yeast extract paste | 0.3 g |
| Potassium mica | 1.2 g; Powder of >200 mesh |
| Rock phosphate | 1.2 g; Powder of >200 mesh |
| Cellulose | 5.0 g; Powder of >200 mesh |
| Autoclaved water | 1000 ml |

It should be noted that the composition of the media provided in Table 11 is not intended to be limiting. Various modifications of the culture medium may be made by those skilled in the art, in view of practical and economic considerations, such as the scale of culture and local supply of media components.

The culturing process may preferably be conducted under conditions in which the concentration of dissolved oxygen is between 0.025 to 0.8 $mol/m^3$, preferably 0.4 $mol/m^3$. The oxygen level can be controlled by any conventional means known to one skilled in the art, including but not limited to stirring and/or bubbling. The process of the invention is carried out at temperatures ranging from about 25° to 30° C.; however, it is preferable to conduct the process at 28° C. The process is initiated in sterilized medium by inoculating typically about 20 ml of each inoculum of the four strains of yeast cells, each at a cell density of about $10^8$ cell/ml. The optional process can be scaled up or down according to needs.

The yeast culture is grown for 12-72 hours, preferably for about 48 hours, in the presence of four independent electromagnetic fields. The electromagnetic fields, which can be applied by a variety of means, each has the following respective frequencies: (1) in the range of about 840 to about 916 MHz for nitrogen-fixing; (2) in the range of about 300 to about 500 MHz for phosphorus-decomposing or phosphorus balancing; (3) in the range of about 100 to about 300 MHz for potassium-decomposing; and (4) in the range of about 1000 to about 1200 MHz for complex carbon-decomposing. Generally, the yeast cells are subjected to an EM field strength in the range from 5 mV/cm to 160 mV/cm per complete cycle. Using an exemplary apparatus as depicted in FIG. 2, the output amplitude of the EM waves used are in the range of 0-3000 mV, preferably 20-1800 mV. The amplitude of each electromagnetic field is repeatedly cycled between 0 mV to 3000 mV, preferably between 20 mV to 1800 mV, in steps of 1 mV at a rate of about two to about ten minutes per complete cycle.

5.12. Soil Adaptation

The yeast cells of the invention must also be able to grow and perform their respective functions in various types of soils. The ability of the yeast cells to survive and grow can be enhanced by adapting the yeast cells of the invention to a particular soil condition.

In another embodiment of the invention, yeast cells prepared according to any one of Sections 5.1-5.10 can be cultured separately or in a mixture in a solid or semi-solid medium containing soil from one or more soil sources. This optional process which can be used to improve the performance of the biological fertilizer described by way of an example as follows.

A suspension containing 10 ml of yeasts at a density of $10^6$ cell/ml is mixed with a 1000 $cm^3$ of the soil medium. The process can be scaled up or down according to needs. The mixture of yeast and soil is cultured for about 48-96 hours, preferably for about 48 hours, in the presence of an electromagnetic field. The electromagnetic field, which can be applied by a variety of means, has a frequency that, depending on the function of the yeasts, corresponds to one of the frequencies described in Sections 5.1-5.10. Generally, the yeast cells are subjected to an EM field strength in the range from 60 mV/cm to 250 mV/cm in this process.

The culture is incubated at temperatures that cycle between about 3° C. to about 48° C. For example, in a typical cycle, the temperature of the culture may start at 35-48° C. and be kept at this temperature for about 1-2 hours, then adjusted up to 42-45° C. and kept at this temperature for 1-2 hours, then adjusted to 26-30° C. and kept at this temperature for about 2-4 hours, and then brought down to 5-10° C. and kept at this temperature for about 1-2 hours, and then the temperature may be raised again to 35-45° C. for another cycle. The cycles are repeated until the process is completed. After the last temperature cycle is completed, the temperature of the culture is lowered to 3-4° C. and kept at this temperature for about 5-6 hours. After adaptation, the yeast cells may be isolated and recovered from the medium by conventional methods, such as filtration. The adapted yeast cells can be stored under 4° C. An exemplary set-up of the culture process is depicted in FIG. 3.

5.13. Separation or Enrichment of Yeast Cells

Yeast cells that have been adapted to form a symbiosis-like relationship according to Section 5.11 can be separated or enriched in such a way that each strain of yeast cells keep their acquired or enhanced functions. Separation of yeast cells is carried out according to methods described in U.S. Pat. No. 5,578,486 and Chinese patent publication CN 1110317A which are incorporated herein by reference in its entirety. The same frequency used for activating the yeast cells may be used during the separation process. The separated yeast cells can then be dried, and stored.

5.14. Manufacture of the Biological Fertilizers

In addition to the yeast cell components, poultry manure and optionally inorganic materials are also included in the biological fertilizer compositions of the invention. The preparation of manure and such materials as well as the steps involved in the manufacture of the biological fertilizer compositions are described below.

5.14.1. Preparation of the Organic and Inorganic Substrate Components

Any poultry manure can be used in the biological fertilizer compositions of the present invention. Mixtures of different kinds of poultry manure can also be used. Organic compounds present in the poultry manure are decomposed by the yeasts of the invention. Depending on the type of manure, in addition to nitrogen, it may contain an useful amount of phosphorus (e.g., $P_2O_5$) and potassium (e.g., $K_2O$). Nutrient concentrations in poultry manure, can vary due to the species and breeds, differences in feeding rations, and methods of storage and moisture content. Methods known in the art can be employed to determine the nutrient value of each batch of poultry manure prior to its use in making a biological fertilizer composition.

Inorganic materials, such as but not limited to phosphate rock and potassium mica, can optionally be included as additional sources of phosphorus and potassium respectively. Other phosphorous- or potassium-containing materials and minerals can also be used. These inorganic compounds are decomposed by K-decomposing and P-decomposing yeast cells into biologically available potassium and biologically available phosphorus that can be used by the growing plants as well as the yeast cells in the fertilizer.

Any inorganic material may be used in combination with poultry manure in the present invention. Alternatively, the inorganic ingredients may be omitted, or substituted by another if it is deemed desirable by the particular application. For example, phosphate rock can be omitted if poultry manure is used which contains sufficient phosphorus biologically available.

The poultry manure is preferably dried to a moisture content of $\leq 5\%$. Both the dried poultry manure and optional inorganic substrate components in the present invention are ground into suitable forms and sizes before incorporated into the fertilizer. Typically, the poultry manure or inorganic material is conveyed into a crusher where it is broken up into pieces of $\leq 5$ cm in diameter. Any conventional crusher or equivalent machines can be used for this purpose. The pieces are then transferred to a grinder by any conveying means and ground to a powder of $\geq 150$ mesh. Any grinder that allows fine grinding can be used for this purpose. The powder is then conveyed to an appropriate storage tank for storage until use with other components of the fertilizer. A schematic illustration of the grinding process is shown in FIGS. 4 and 5.

5.14.2. Fermentation Process Using Growth Factor-Producing Yeast

In the present invention, the preparation of GF-producing yeast is carried out in a fermentation process using as seed the activated yeast strain as described in Section 5.6. A schematic of the fermentation process is illustrated in FIG. 6.

The fermentation medium is prepared according to a ratio of 2.5 liters of water per kilogram of starch. Clean water, preferably water free of any microorganisms, is used to prepare the fermentation medium. The fermentation is carried out at a temperature between 20-30° C., preferably between 25-28° C., in a clean environment and in a space where there are no strong sources of electromagnetic fields, such as power lines and power generators. Any equipments that contact the fermentation broth, including reactors, pipelines, and stirrers, must be throughly cleaned before each use. The fermentation process normally lasts about 48-72 hours at 28-30° C. when at least 90% of the fermentation substrate is fermented. Fermentation is preferably conducted under semi-aerobic conditions or conditions in which the oxygen level is about 20-60% of the maximal soluble oxygen concentration. The oxygen level can be controlled by any conventional means known to one skilled in the art, including but not limited to stirring and/or bubbling. After fermentation, the cell counts should reach about $2\times10^{10}$ cells/ml. The fermentation broth is kept at a temperature in the range of 15-28° C. and must be used within 24 hours. Alternatively, the GF-producing yeasts can be drained, dried and stored in powder form.

5.14.3. Fermentation Process Using ATP-Producing Yeast

In the present invention, the preparation of ATP-producing yeast is carried out by a fermentation process using as seed the adapted yeast strain as described in Section 5.7. A schematic of the fermentation process is illustrated in FIG. 6.

The fermentation medium is prepared according to a ratio of 2.5 liters of water per kilogram of starch. Clean water, preferably water free of any microorganisms, most preferably autoclaved water, is used to prepare the fermentation media. The fermentation is carried out at a temperature between 20-30° C., preferably between 25-28° C., in a clean environment and in a space where there are no strong sources of electromagnetic fields, such as power lines and power generators. Any equipments that contact the fermentation broth, including reactors, pipelines, and stirrers, must be throughly cleaned before each use. The fermentation process normally lasts about 48-72 hours, depending on the fermentation temperature. Preferably at the end of the process at least 90% of the fermentation substrate is fermented. Fermentation is preferably conducted under semi-aerobic conditions or conditions in which the oxygen level is about 20-60% of the maximal soluble oxygen concentration. The oxygen level can be controlled by any conventional means known to one skilled in the art, including but not limited to stirring and/or bubbling. After fermentation, the cell counts should reach about $2\times10^{10}$ cells/ml. The fermentation broth is kept at a temperature in the range of 15-28° C. and must be used within 24 hours. Alternatively, the ATP-producing yeasts can be drained, dried and stored in powder form.

5.14.4. Preparation of Mixture of Raw Materials

Poultry manure and the optional inorganic raw materials are mixed in exemplary proportions as shown in Table 12. Appropriate amount of organic and inorganic materials prepared according to Section 5.10.1 and starch are conveyed to a mixer. Any conventional mixer, such as but not limited a rotary drum mixer, can be used. The mixing tank is rotated constantly so that powders of poultry manure and starch are mixed evenly. The mixture is then conveyed to a storage tank. The procedure for mixing poultry manure and inorganic substrate material is illustrated in FIG. 7.

TABLE 12

Ratio of raw materials

| Material | Percentage | Requirement |
|---|---|---|
| Powder of poultry manure | 58-63% | ≧150 mesh, water content ≦5% |
| Powder of inorganic materials | 20% | ≧150 mesh, water content ≦3% |
| Starch | 10-15% | regular starch powder, water content ≦8% |

5.14.5. Preparation of Yeast Mixture

If no inorganic materials is used, the proportion of poultry manure can be increased up to 80%. A yeast mixture is prepared in the exemplary proportions as shown in Table 13. Appropriate amounts of the nine yeast strains in dried powder form prepared according to Section 5.1-5.10 are conveyed to a mixing tank. The yeasts are allowed to mix for about 10-20 minutes. The mixture is then transferred to a storage tank. Any equipments used for mixing yeasts, including the mixing tank and the storage tank, must be throughly cleaned, preferably sterilized, before each use. The yeast mixture is stored at a temperature below 20° C. and must be used within 24 hours. The procedure for mixing yeasts is illustrated in FIG. 8. Alternatively, the mixture of nine yeasts can be dried and stored in powder form.

TABLE 13

Ratio of microorganisms

| Yeast | Quantity | Percentage (dry weight) | Note |
|---|---|---|---|
| Nitrogen-fixing yeast | 1.0-2.0 kg | 0.1-0.2% | Dry yeast powder |
| Phosphorus-decomposing yeast | 1.0-2.0 kg | 0.1-0.2% | Dry yeast powder |
| Potassium-decomposing yeast | 1.0-2.0 kg | 0.1-0.2% | Dry yeast powder |
| Carbon-decomposing yeast | 1.0-2.0 kg | 0.1-0.2% | Dry yeast powder |
| Pathogen-suppressing yeast | 1.0-2.0 kg | 0.1-0.2% | Dry yeast powder |
| Chemical-decomposing yeast | 1.0-2.0 kg | 0.1-0.2% | Dry yeast powder |
| Odor-reducing yeast | 1.0-2.0 kg | 0.1-0.2% | Dry yeast powder |
| Growth factor-producing yeast | 25 L | 1% | Yeast fermentation broth |
| ATP-producing yeast | 75 L | 3% | Yeast fermentation broth |

5.14.6. Manufacture of Biological Fertilizer

The biological fertilizer of the present invention is produced by mixing the yeast mixture of Section 5.14.5 and the mixture of the organic and inorganic materials of Section 5.14.1 at a ratio according to Table 14. For example, the yeasts and the poultry manure, and inorganic materials are conveyed to a granulizer to form granules. The granules of the fertilizer are then dried in a two-stage drying process. During the first drying stage, the fertilizer is dried in a first dryer at a temperature not exceeding 65° C. for a period of time not exceeding 10 minutes so that yeast cells quickly become dormant. The fertilizer is then send to a second dryer and dried at a temperature not exceeding 70° C. for a period of time not exceeding 30 minutes to further remove water. After the two stages, the water content should be lower than 5%. It is preferred that the temperatures and drying times be adhered to in both drying stages so that yeast cells do not lose their vitality and functions. The fertilizer is then cooled to room temperature. The fertilizer may also be screened in a separator so that fertilizer granules of a preferred size are selected. Any separator, such as but not limited to a turbo separator with adjustable speed and screen sizes, can be used. The fertilizer of the selected size is then sent to a bulk bag filler for packing.

The production process is illustrated in FIGS. 9-11. FIG. 9 is a schematic illustration of the procedure for producing the fertilizer from its components. FIG. 10 is a schematic illustration of the drying process. FIG. 11 is a schematic illustration of the cooling and packing process.

TABLE 14

Composition of the biological fertilizer (for one metric ton of fertilizer)

| | Quantity | Percentage (dry weight) | Note |
|---|---|---|---|
| Mixture of raw materials | 952-956 kg | 95.2-95.4% | Dry weight |
| Mixture of yeasts | 100 L | 4.4-4.8% | Dry weight |

6. EXAMPLE

The following examples demonstrate the manufacture of an exemplary biological fertilizer composition of the present invention. These examples represent a preferred embodiment of the present invention.

6.1 Biological Fertilizer Composition Comprising Poultry Manure

*Saccharomyces cerevisiae* strains having accession numbers AS2.628, AS2.631, AS2.982, AS2.413 and AS2.536 are used to prepare the yeast cell components of the biological fertilizer composition. All were deposited in China General Microbiological Culture Collection Center (CGMCC), China Committee for Culture Collection of Microorganisms. Yeast strain AS2.628 is cultured according to the method described in Section 5.1 for nitrogen-fixation; and to the method described in Section 5.3 for P-balancing. Yeast strain AS2.631 is cultured according to the method described in Section 5.4 for K-decomposition. Yeast strain AS2.982 is cultured according to the method described in Section 5.5 for C-decomposition. Yeast strain AS2.413 is cultured according to the method described in Section 5.6 for production of growth factor. Yeast strain AS2.536 is cultured according to the method described in Section 5.7 for ATP production. Yeast strain IFFI1221 is cultured according to the method described in Section 5.8 for suppressing growth of pathogens. Yeast strain IFFI1293 is cultured according to the method described in Section 5.9 for degrading undesirable chemicals. Yeast strain AS2.607 is cultured according to the method described in Section 5.10 for odor reduction.

The poultry manure in powder form is prepared according to Section 5.14.1.

The production of growth factor-producing yeast is carried out in a fermentation process using as seed the activated yeast strain AS2.413 as described in Section 5.6. A schematic of the fermentation process is illustrated in FIG. 6. The fermentation medium is prepared according to a ratio of 2.5 liters of clean water per kilogram of starch and 10 kilograms of starch per metric ton of biological fertilizer. The fermentation medium is inoculated according to a ratio of 10 ml of seed solution per liter of medium. The fermentation is carried out at a temperature of 28±1° C. and an oxygen concentration of 0.4 mol/m³ in a clean environment where there were no sources of electromagnetic fields. After about 48 hours of fermentation, the concentration of yeast cells reached about 2×10¹⁰ cells/ml.

The production of ATP-producing yeast is carried out in a fermentation process using as seed the activated yeast strain AS2.536 as described in Section 5.7. A schematic of the fermentation process is illustrated in FIG. 6. The fermentation medium is prepared according to a ratio of 2.5 liters of clean water per kilogram of starch and 10 kilograms of starch per metric ton of biological fertilizer. The fermentation medium is inoculated according to a ratio of 10 ml of seed solution per liter of medium. The fermentation is carried out at a temperature of 28±1° C. and an oxygen concentration of 0.4 mol/m³ for about 56 hours in a clean environment where there were no sources of electromagnetic fields. After fermentation, the cell counts reached about 2×10¹⁰ cells/ml.

The mixture of raw materials is prepared according to Table 15 and the procedure in Section 5.14.4.

TABLE 15

Ratio of raw materials

| Material | Percentage | Requirement |
|---|---|---|
| Powder of dried poultry manure | 80.3% | ≧150 mesh, water content ≦5% |
| Starch | 15% | regular starch powder, water content ≦8% |

The yeast mixture is prepared according to Table 15 and the procedure described in Section 5.14.5.

TABLE 16

Ratio of yeasts (for 1 metric ton of fertilizer)

| Yeast | Quantity | Percentage (dry weight) | Note |
|---|---|---|---|
| Nitrogen-fixing yeast AS2.628 | 2.0 kg | 0.2% | Dry yeast powder |
| Phosphorus-balancing yeast AS2.628 | 2.0 kg | 0.2% | Dry yeast powder |
| Potassium-decomposing yeast AS2.631 | 2.0 kg | 0.2% | Dry yeast powder |
| Carbon-decomposing yeast AS2.982 | 2.0 kg | 0.2% | Dry yeast powder |
| Pathogen-suppressing yeast IFFI1221 | 1.0-2.0 kg | 0.1-0.2% | Dry yeast powder |
| Chemical-degrading yeast IFFI1293 | 1.0-2.0 kg | 0.1-0.2% | Dry yeast powder |
| Odor-reducing yeast AS2.607 | 1.0-2.0 kg | 0.1-0.2% | Dry yeast powder |
| Growth factor producing yeast AS2.413 | 25 L | 1% | Yeast fermentation broth |
| ATP producing yeast AS2.536 | 75 L | 3% | Yeast fermentation broth |

The biological fertilizer is produced by mixing the yeast mixture, the organic materials at a ratio according to Table 17. The mixed yeasts and organic materials were conveyed to a granulizer to form granules. The granules of the fertilizer were then dried in a two stage drying process. During the first drying stage, the fertilizer is dried in a first dryer at a temperature not exceeding 60±2° C. for a period of 5 minutes so that yeast cells quickly became dormant. The fertilizer is then sent to a second dryer and dried at a temperature not exceeding 65±2° C. for a period of 8 minutes to further remove water. The fertilizer is then cool to room temperature. The fertilizer is then sent to a bulk bag filler for packing.

TABLE 17

Fertilizer composition (for 1 metric ton of fertilizer)

| | Quantity | Percentage (dry weight) | Note |
|---|---|---|---|
| Raw material mixture | 949 kg | 94.9% | Dry weight |
| Yeast mixture | 100 L | 5.1% | Dry weight |

The present invention is not to be limited in scope by the specific embodiments described which are intended as single illustrations of individual aspects of the invention, and functionally equivalent methods and components are within the scope of the invention. Indeed various modifications of the invention, in addition to those shown and described herein will become apparent to those skilled in the art from the foregoing description and accompanying drawings. Such modifications are intended to fall within the scope of the appended claims.

What is claimed is:

1. A method for enhancing plant growth comprising growing a plant in the presence of a biological fertilizer composition, wherein said biological fertilizer composition comprises:
    (I) poultry manure;
    (II) at least one of the following:
        (a) a first yeast prepared by culturing a first plurality of yeast cells in a first electromagnetic field having a frequency in the range of 840 to 916 MHz and a field strength of 10 to 200 mV/cm;
        (b) a second yeast prepared by culturing a second plurality of yeast cells in a second electromagnetic field having a frequency in the range of 300 to 500 MHz and a field strength of 10 to 300 mV/cm;
        (c) a third yeast prepared by culturing a third plurality of yeast cells in a third electromagnetic field having a frequency in the range of 190 to 285 MHz and a field strength of 10 to 200 mV/cm; and
    (III) at least one of the following:
        (d) a fourth yeast prepared by culturing a fourth plurality of yeast cells in a fourth electromagnetic field having a frequency in the range of 30 to 50 MHz and a field strength of 20 to 200 mV/cm;
        (e) a fifth yeast prepared by culturing a fifth plurality of yeast cells in a fifth electromagnetic field having a frequency in the range of 70 to 100 MHz and a field strength in the range of 40 to 250 mV/cm; and
        (f) a sixth yeast prepared by culturing a sixth plurality of yeast cells in a sixth electromagnetic field having a frequency in the range of 2160 to 2250 MHz and 2280 to 2380 MHz and a field strength in the range of 100 to 300 mV/cm.

2. The method of claim 1, wherein the biological fertilizer composition is applied to soil at the depth of the major root system of the plant.

3. The method of claim 1, wherein about 600 to 1350 kg/ha of the biological fertilizer composition is used.

4. The method of claim 1, wherein the plant is a cereal crop, a vegetable crop, a fruit crop, a flower crop, or a grass crop.

5. The method of claim 1, wherein the plant is wheat, barley, corn, soybean, rice, oat, potato, apple, orange, tomato, melon, cherry, lemon, lettuce, carrot, sugar cane, tobacco, or cotton.

6. The method of claim 1, wherein the yeast (b) is prepared by culturing a second plurality of yeast cells in a second electromagnetic field having a frequency in the range of 380 to 485 MHz and a field strength of 90 to 300 mV/cm.

7. The method of claim 1, wherein the biological fertilizer composition further comprise at least one of the following:
(g) a seventh yeast prepared by culturing a seventh plurality of yeast cells in a fourth electromagnetic field having a frequency in the range of to 1050 to 1160 MHz and a field strength of 10 to 200 mV/cm;
(h) an eighth yeast prepared by culturing an eighth plurality of yeast cells in an eighth electromagnetic field having a frequency in the range of 1340 to 1440 MHz and a field strength of 20 to 200 mV/cm; and
(i) a ninth yeast prepared by culturing a ninth plurality of yeast cells in a ninth electromagnetic field having a frequency in the range of 1630 to 1730 MHz and a field strength of 20 to 200 mV/cm.

8. The method of claim 1 or 7, wherein each yeast comprises yeast cells of the genus *Saccharomyces*.

9. The method of claim 1 or 7, wherein each yeast separately comprises cells of a species of yeast selected from the group consisting of *Saccharomyces cerevisiae, Saccharomyces chevalieri, Saccharomyces exiguus, Saccharomyces logos, Saccharomyces oviformis, Saccharomyces sake, Saccharomyces uvarum Beijer, Saccharomyces willianus, Saccharomyces ludwigii, Saccharomyces sinenses*, and *Saccharomyces carlsbergensis*.

10. The method of claim 1 or 7, wherein each yeast separately comprises cells of a strain of yeast selected from the group consisting of *Saccharomyces cerevisiae* Hansen, ACCC2034, ACCC2035, ACCC2036, ACCC2037, ACCC2038, ACCC2039, ACCC2040, ACCC2041, ACCC2042, AS2.1, AS2.4, AS2.11, AS2.16, AS2.56, AS2.69, AS2.70, AS2.93, AS2.98, AS2.101, AS2.109, AS2.110, AS2.112, AS2.139, AS2.173, AS2.174, AS2.182, AS2.196, AS2.242, AS2.336, AS2.374, AS2.375, AS2.379, AS2.380, AS2.382, AS2.390, AS2.393, AS2.395, AS2.396, AS2.397, AS2.398, AS2.400, AS2.406, AS2.408, AS2.409, AS2.413, AS2.414, AS2.415, AS2.416, AS2.422, AS2.423, AS2.431, AS2.432, AS2.451, AS2.452, AS2.453, AS2.458, AS2.460, AS2.463, AS2.467, AS2.486, AS2.502, AS2.503, AS2.504, AS2.516, AS2.535, AS2.536, AS2.558, AS2.560, AS2.561, AS2.562, AS2.576, AS2.593, AS2.594, AS2.614, AS2.620, AS2.628, AS2.631, AS2.666, AS2.982, AS2.1190, AS2.1364, AS2.1396, IFFI1001, IFFI1002, IFFI1005, IFFI1006, IFFI1008, IFFI1009, IFFI1010, IFFI1012, IFFI1021, IFFI1027, IFFI1037, IFFI1042, IFFI1043, IFFI1045, IFFI1048, IFFI1049, IFFI1050, IFFI1052, IFFI1059, IFFI1060, IFFI1063, IFFI1202, IFFI1203, IFFI1206, IFFI1209, IFFI1210, IFFI1211, IFFI1212, IFFI1213, IFFI1215, IFFI1220, IFFI1221, IFFI1224, IFFI1247, IFFI1248, IFFI1251, IFFI1270, IFFI1277, IFFI1287, IFFI1289, IFFI1290, IFFI1291, IFFI1292, IFFI1293, IFFI1297, IFFI1300, IFFI1301, IFFI1302, IFFI1307, IFFI1308, IFFI1309, IFFI1310, IFFI1311, IFFI1331, IFFI1335, IFFI1336, IFFI1337, IFFI1338, IFFI1339, IFFI1340, IFFI1345, IFFI1348, IFFI1396, IFFI1397, IFFI1399, IFFI1411, IFFI1413; *Saccharomyces cerevisiae* Hansen var. *ellipsoideus* (Hansen) Dekker, ACCC2043, AS2.2, AS2.3, AS2.8, AS2.53, AS2.163, AS2.168, AS2.483, AS2.541, AS2.559, AS2.606, AS2.607, AS2.611, AS2.612; *Saccharomyces chevalieri* Guillermond, AS2.131, AS2.213; *Saccharomyces exiguus* Hansen, AS2.349, AS2.1158; *Saccharomyces logos* van laer et Denamur ex Jorgensen, AS2.156, AS2.327, AS2.335; *Saccharomyces oviformis* Osterwalder, AS2.100; *Saccharomyces sake* Yabe, ACCC2045; *Saccharomyces carlsbergensis* Hansen, ACCC2032, ACCC2033, AS2.113, AS2.116, AS2.118, AS2.121, AS2.132, AS2.162, AS2.189, AS2.200, AS2.216, AS2.265, AS2.377, AS2.417, AS2.420, AS2.440, AS2.441, AS2.443, AS2.444, AS2.459, AS2.595, AS2.605, AS2.638, AS2.742, AS2.745, AS2.748, AS2.1042; *Saccharomyces uvarum* Beger, IFFI1023, IFFI1032, IFFI1036, IFFI1044, IFFI1072, IFFI1205, IFFI1207; *Saccharomyces willianus* Saccardo, AS2.5, AS2.7, AS2.119, AS2.152, AS2.293, AS2.381, AS2.392, AS2.434, AS2.614, AS2.1189; *Saccharomyces* sp., AS2.311; *Saccharomyces ludwigii* Hansen, ACCC2044, AS2.243, AS2.508; and *Saccharomyces sinenses* Yue, AS2.1395.

11. The method of claim 1 or 7, wherein each yeast comprises cells of *Saccharomyces cerevisiae*.

12. The method of claim 1 or 7, wherein the biological fertilizer composition further comprises an inorganic substrate component.

13. The method of claim 1 or 7, wherein the inorganic substrate component comprises one or more of rock phosphate, apatite, phosphorite, sylvinite, halite, camalitite, or potassium mica.

14. The method of claim 1 or 7, wherein the yeast cells are dried.

15. The method of claim 7, wherein the biological fertilizer composition is applied to soil at the depth of the major root system of the plant.

16. The method of claim 7, wherein about 600 to 1350 kg/ha of the biological fertilizer composition is used.

17. The method of claim 7, wherein the plant is a cereal crop, a vegetable crop, a fruit crop, a flower crop, or a grass crop.

18. The method of claim 7, wherein the plant is wheat, barley, corn, soybean, rice, oat, potato, apple, orange, tomato, melon, cherry, lemon, lettuce, carrot, sugar cane, tobacco, or cotton.

19. The method of claim 7, wherein the yeast (b) is prepared by culturing a second plurality of yeast cells in a second electromagnetic field having a frequency in the range of 380 to 485 MHz and a field strength of 90 to 300 mV/cm.

20. The method of claim 7, wherein the biological fertilizer composition comprises yeasts (a) through (f) of claim 1, and yeasts (g) through (i) of claim 7.

21. The method of claim 7, wherein yeast (a) comprises cells of the yeast *Saccharomyces cerevisiae* AS2.628; yeast (b) comprises cells of the yeast *Saccharomyces cerevisiae* AS2.399; yeast (c) comprises cells of the yeast *Saccharomyces cerevisiae* AS2.631; yeast (d) comprises cells of one or more of the following yeast *Saccharomyces cerevisiae* IFFI1037, IFFI1021, IFFI1331, IFFI1345, or IFFI1211, yeast (e) comprises cells of one or more of the following yeast *Saccharomyces cerevisiae* AS2.293, IFFI1063, IFFI1221, IFFI1340, IFFI1215, IFFI1213, IFFI1206, IFFI1211, IFFI1210, or IFFI1260; and yeast (f) comprises cells of one or more of the following yeast *Saccharomyces cerevisiae* AS2.559, AS2.423, AS2.612, AS2.53, or AS2.163.

22. The method of claim 20, wherein yeast (a) comprises cells of the yeast *Saccharomyces cerevisiae* AS2.628; yeast (b) comprises cells of the yeast *Saccharomyces cerevisiae* AS2.399; yeast (c) comprises cells of the yeast *Saccharomyces cerevisiae* AS2.631; yeast (d) comprises cells of one or more of the following yeast *Saccharomyces cerevisiae* IFFI1037, IFFI1021, IFFI1331, IFFI1345, or IFFI1211; yeast component (e) comprises cells of one or more of the following yeast *Saccharomyces cerevisiae* AS2.293, IFFI1063, IFFI1221, IFFI1340, IFFI1215, IFFI1213, IFFI1206, IFFI1211, IFFI1210, yeast (f) comprises cells of one or more of the following yeast *Saccharomyces cerevisiae* AS2.559, AS2.423, AS2.612, AS2.53, or AS2.163; yeast (g) comprises cells of the yeast *Saccharomyces cerevisiae* AS2.982; yeast (h) comprises cells of the yeast *Saccharomyces cerevisiae* AS2.413; and yeast (i) comprises cells of the yeast *Saccharomyces cerevisiae* AS2.536.

* * * * *